United States Patent
Tarnopolsky

(10) Patent No.: US 11,167,001 B2
(45) Date of Patent: Nov. 9, 2021

(54) WEIGHT MANAGEMENT COMPOSITION

(71) Applicant: Exerkine Corporation, Hamilton (CA)

(72) Inventor: Mark Tarnopolsky, Hamilton (CA)

(73) Assignee: Exerkine Corporation, Ontario (CA)

(*) Notice: Subject to any disclaimer, the term of this patent is extended or adjusted under 35 U.S.C. 154(b) by 0 days.

(21) Appl. No.: 16/528,855

(22) Filed: Aug. 1, 2019

(65) Prior Publication Data

US 2019/0350997 A1    Nov. 21, 2019

Related U.S. Application Data

(63) Continuation of application No. PCT/CA2019/050342, filed on Mar. 20, 2019.

(60) Provisional application No. 62/645,561, filed on Mar. 20, 2018.

(51) Int. Cl.
| | |
|---|---|
| A61K 36/82 | (2006.01) |
| A61P 3/04 | (2006.01) |
| A61K 31/122 | (2006.01) |
| A61K 31/197 | (2006.01) |
| A61K 31/201 | (2006.01) |
| A61K 31/352 | (2006.01) |
| A61K 31/355 | (2006.01) |
| A61K 31/385 | (2006.01) |
| A61K 36/21 | (2006.01) |
| A61K 36/61 | (2006.01) |
| A61K 36/74 | (2006.01) |
| A61K 45/06 | (2006.01) |

(52) U.S. Cl.
CPC ............ *A61K 36/82* (2013.01); *A61K 31/122* (2013.01); *A61K 31/197* (2013.01); *A61K 31/201* (2013.01); *A61K 31/352* (2013.01); *A61K 31/355* (2013.01); *A61K 31/385* (2013.01); *A61K 36/21* (2013.01); *A61K 36/61* (2013.01); *A61K 36/74* (2013.01); *A61K 45/06* (2013.01); *A61P 3/04* (2018.01)

(58) Field of Classification Search
None
See application file for complete search history.

(56) References Cited

FOREIGN PATENT DOCUMENTS

| | | |
|---|---|---|
| CA | 2751218 A1 | 2/2013 |
| EP | 2250911 A1 | 11/2010 |
| FR | 2712191 A1 | 5/1995 |
| WO | 2006/096996 A1 | 9/2006 |
| WO | 2009/006366 A2 | 1/2009 |
| WO | 2012/013975 A1 | 2/2012 |
| WO | 2013/113027 A2 | 8/2013 |
| WO | 2016/004363 A2 | 1/2016 |
| WO | 2017/155898 A1 | 10/2017 |

OTHER PUBLICATIONS

Lieberman, S., Alternative & Complementary Therapies, 10:330. (Year: 2004).*
Shixian, Q., et al., J. Med. Food, 9:451. (Year: 2006).*
Song, et al., Evidence-Based Complementary and Alternative Medicine, "Decaffeinated Green Coffee Bean Extract Attenuates Diet-Induced Obesity and Insulin Resistance in Mice," pp. 1-14. (Year: 2014).*
Zielinska-Przyjemska, et al., Phytotherapy Research, 23:49. (Year: 2009).*
Sohet, et al., Biochemical Pharmacology, 78:1391. (Year: 2009).*
Kim, et al., Nature Medicine, 10:727. (Year: 2004).*
Shen, et al., Experimental Biology and Medicine, 235:47. (Year: 2010).*
Uchiyama, et al., Nutrition, 27:287. (Year: 2011).*
Blankson, et al., The Journal of Nutrition, 130:2943. (Year: 2000).*
Kazak, et al., Cell, 163:643. (Year: 2015).*
Bhathena, et al., The American Journal of Clinical Nutrition, 76:1191. (Year: 2002).*
International Search Report—PCT/CA2019/050342 dated May 29, 2019.
Written Opinion of the International Searching Authority—PCT/CA2019/050342 dated May 29, 2019.

* cited by examiner

*Primary Examiner* — Michael Barker
(74) *Attorney, Agent, or Firm* — Susan Tandan; Gowling WLG (Canada) LLP

(57) ABSTRACT

A method for promoting weight management in a mammal is provided, comprising administering to the mammal a weight loss agent and a mitochondria enhancing agent. Compositions for weight management are also provided.

22 Claims, 21 Drawing Sheets

A

B

C

D

WEIGHT MANAGEMENT COMPOSITION

FIELD OF THE INVENTION

The present invention generally relates to a composition and method for improving the health of an individual, and more particularly relates to a composition and method for promoting weight management in an individual.

BACKGROUND OF THE INVENTION

The epidemic of overweight and obesity has become one of the most significant health concerns faced at the global level. Over the past thirty years, the prevalence of obesity has almost tripled in number, to the extent that globally, approximately 40% of adults 18 years of age and older are now overweight and around 13% are obese. It is well established that the presence of obesity is associated with the development of numerous other diseases, such as fatty liver disease, cardiovascular disease, type 2 diabetes, hypertension, dyslipidemia, gallbladder disease, osteoarthritis, sleep apnea, asthma, chronic kidney disease and depression. Obesity is caused by an imbalance between total energy expenditure and energy intake in an individual. Accordingly, each of these obesity-associated comorbidities can be prevented or treated by weight loss.

One of the most potent strategies available for reducing body weight is to participate in a structured program of physical activity, such as endurance or resistance exercise training. Studies conducted over the past several decades have repeatedly shown that exercise or physical activity increase energy expenditure to promote weight loss and improve health, however a large portion of the population in most countries is not active at recommended levels. Primary reasons for which individuals do not engage in exercise include that it is inconvenient, costly, time consuming, difficult to perform, boring or otherwise unenjoyable.

Consuming a healthy, well-balanced diet without excessive portion size is method of reducing energy intake to promote fat loss and maintain a state of good health. Similar to exercise, however, there are many barriers to eating a healthy diet, such as a lack of access to, greater cost of, and greater time commitment required to prepare it, as well as the unpalatability of many healthy foods or meals in comparison to less healthy alternatives. Furthermore, even when weight loss is achieved by diet and exercise, the amount of fat loss is often inadequate to meet the full amount of weight loss desired by an individual to maintain optimal health.

It would be desirable, thus, to provide an improved weight management composition and method for improving the health of an individual.

SUMMARY OF THE INVENTION

A weight management composition has now been developed which has been determined to promote weight loss in an individual.

Thus, in a first aspect of the present invention, a weight management composition comprising a weight loss agent and a mitochondria enhancing agent is provided.

In one embodiment, a weight management composition comprising a weight loss agent and a mitochondria enhancing agent is provided, wherein the weight loss agent comprises green tea extract, green coffee bean extract and forskolin and the mitochondria enhancing agent comprises beet root extract, coenzyme Q10, alpha lipoic acid and vitamin E.

In another aspect of the invention, a method is provided for promoting weight management in a mammal comprising the step of administering to the mammal a weight management composition comprising a weight loss agent and a mitochondria enhancing agent.

In another aspect, a method is provided to treat or improve at least one of the following in a mammal: body weight, body fat, mitochondrial capacity, fatty liver disease, dyslipidemia, oxidative stress levels, brown adipose tissue activity and systemic inflammation levels comprising administering to the mammal a composition comprising a weight loss agent and a mitochondria enhancing agent.

These and other aspects of the present invention will become apparent in the detailed description that follows, by reference to the following figures.

DETAILED DESCRIPTION OF THE INVENTION

Figure 1:
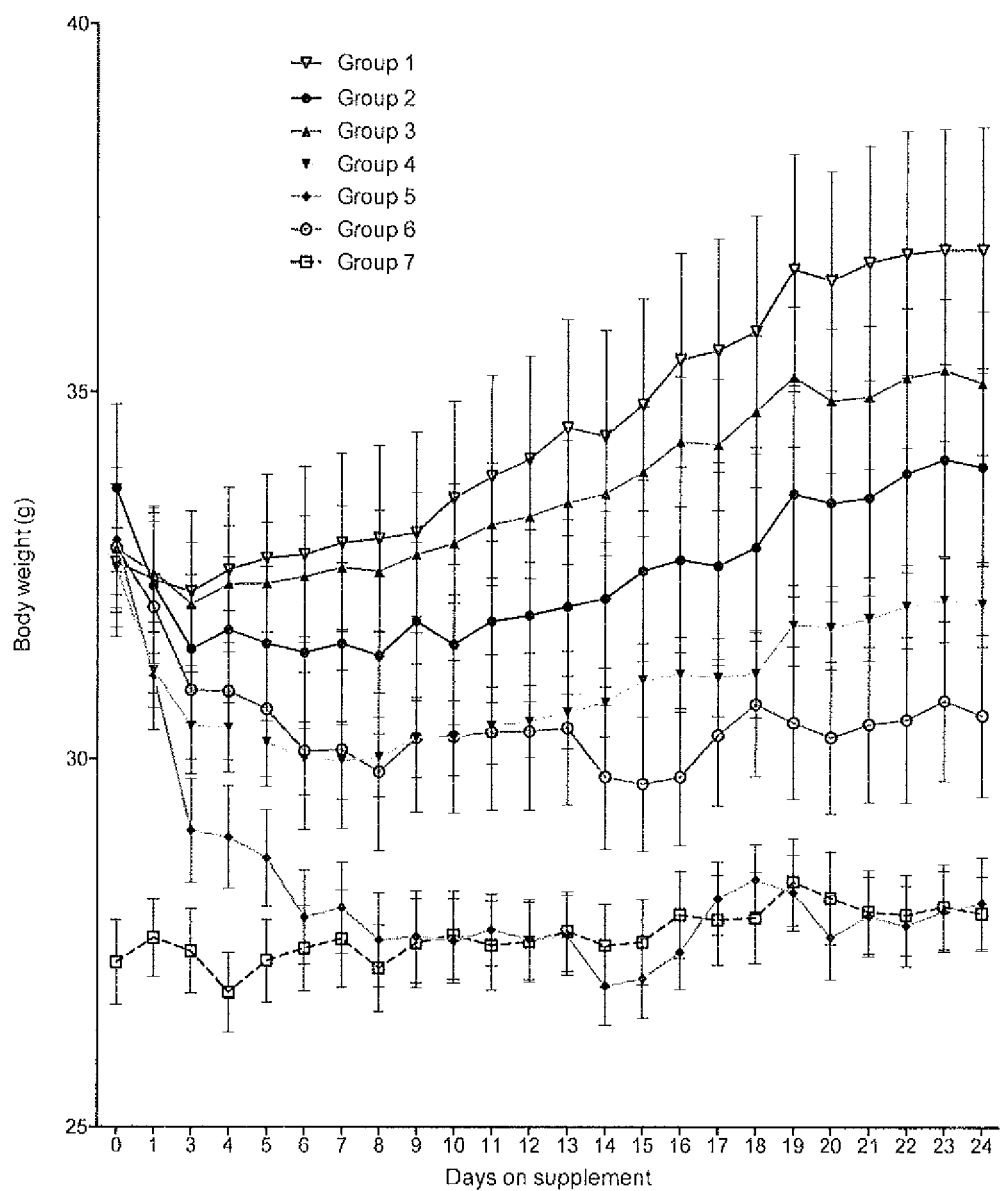
FIG. 1 graphically illustrates the body weight of mice fed a weight management composition or a control diet and allocated to either sedentary or exercise training conditions for 30 days.

A weight management composition comprising a weight loss agent and a mitochondria enhancing agent is provided which is useful to treat or improve aspects of the health of a mammal such as weight management, mitochondrial capacity, fatty liver disease, dyslipidemia, oxidative stress levels, brown adipose tissue (BAT) activity and systemic inflammation levels.

The term "weight management" is used herein to refer to achieving, progressing towards or maintaining a body weight within a normal healthy range. One of the most widely used metrics for measuring body weight is the "body mass index" or BMI. A BMI range of about 18.5 to 24.9 is considered to be the normal healthy range for the BMI index, e.g. a body weight within a range that promotes the health, fitness, well-being and physical appearance of an individual. Overweight and obesity are defined as the abnormal or excessive accumulation of fat that may cause health impairments. An individual having a BMI between about 25-29.9 is generally considered to be overweight, while an individual having a BMI equal to or greater than 30 is generally considered to be obese. Weight management may also refer to the maintenance of body fat levels within a healthy range, e.g. a body fat percentage within a range that promotes the health, fitness, well-being and physical appearance of an individual. An example of a healthy body fat range may be an amount ranging from the essential body fat level (i.e. the amount considered essential for physical and psychological well-being) up to approximately 20% above the essential body fat level. According to the American Council on Exercise, the amount of fat considered to be essential for men is about 2-5% of body fat and for women is about 10-13% body fat.

The weight management composition comprises at least one weight loss agent. The weight loss agent may be any suitable agent that possesses the characteristic of promoting weight loss in a mammal, e.g. by at least about 0.5%, and preferably a body weight reduction of about 1% or more, e.g. by 5%, 10%, 30%, 50%, 70% or greater of body weight in the individual prior to treatment with the present composition, or a reduction in the rate of rising body weight by at least about 1% or more, and preferably a reduction of about 5% or more, e.g. by 10%, 30%, 50%, 70%, 90% or greater to the rate of body weight increase prior to treatment. Suitable weight loss agents may promote weight loss by any one or more of several mechanisms including, but not limited to, the following: decreasing food intake or promoting satiety, decreasing lipid absorption, increasing energy expenditure, decreasing pre-adipocyte differentiation and proliferation, decreasing lipogenesis or increasing lipolysis or lipid oxidation. Examples of weight loss agents include, but are not limited to, chitosan, psyllium, guar gum, capsaicin, caffeine, *Garcina cambogia, Pinus densiflora*, capsaicin, yohimbe, hoodia, glucomannan, African mango, guarana, pyruvate, carnitine, beta-glucans, fucoxanthin, raspberry ketone, white kidney bean, kola nut, chromium, ginseng, psyllium, St. John's wort, dandelion, hydroxycitric acid, conjugated linoleic acid, green tea extract, black tea extract, green coffee bean extract, forskolin, bitter orange and mixtures thereof.

In one embodiment, the weight loss agent comprises a mixture of green tea extract, green coffee bean extract and forskolin.

In another embodiment, the weight loss agent comprises a mixture of green tea extract, black tea extract, green coffee bean extract, conjugated linoleic acid and forskolin.

Green tea extract for use in the present composition may be selected from any suitable green tea leaf or green tea source such as Sencha, Fukamushi Sencha, Gyokuro, Kabusecha, Matcha, Tencha, Genmaicha, Matcha, Shincha, Hojicha, Ichibanchagreen, Nibancha and Sanbancha tea, which are derived from the *Camellia sinensis* leaf. Green tea is abundant in polyphenols such as catechins. Examples of such catechins include epigallocatechin gallate, catechin, catechin gallate, epicatechin, gallocatechin, epigallocatechin, and epicatechin gallate. Preferably, the green tea extract for use in the composition comprises about 80% or more of catechins by dry weight, with about 50% or more of the catechins being epigallocatechin gallate. Green tea extract for use in the present composition may be either caffeinated or substantially decaffeinated, for example, having less than 1% caffeine by dry weight. In one embodiment, the green tea extract comprises about 0.1-90% of the dry weight of the weight management composition, such as about 5-50%, or about 10-30% of the dry weight of the composition. In another embodiment, the weight management composition comprises a daily dosage of about 10 mg-5 g of green tea extract and preferably, about 50-1000 mg.

Green coffee bean extract for use in the present composition may be selected from any suitable green coffee bean source such as *Coffea Arabica* or *Coffea canephora*. Green coffee beans contain several types of chlorogenic acids, such as 3-caffeoylquinic acid, 4-caffeoylquinic acid and 5-caffeoylquinic acid. Preferably, the green coffee bean extract for use in the present composition comprises about 30% or more of chlorogenic acids by dry weight. Green coffee bean extract for use in the present composition may be either caffeinated or substantially decaffeinated, for example, having less than 1% of caffeine by dry weight. Preferably the green coffee bean extract comprises at least 35% chlorogenic acids and at least 35% caffeine by dry weight. In one embodiment, the green coffee bean extract comprises about 0.1-80% of the dry weight of the weight management composition, such as about 5-50%, or about 10-30% of the dry weight of the composition. In another embodiment, the weight management composition comprises a daily dosage of about 10 mg-5 g of green coffee bean extract and preferably, about 50-1000 mg.

Forskolin for use in the present composition may be obtained from any suitable source. Forskolin may be extracted from the *Coleus forskohli* plant, or synthetically produced. Preferably, the forskolin extract is derived from the *Coleus forskohli* plant and is standardized to contain about 40% forskolin. In one embodiment, forskolin comprises about 0.05-50% of the dry weight of the weight management composition, such as about 0.1-30%, or about 0.5-10% of the dry weight of the composition. In another embodiment, the weight management composition comprises a daily dosage of about 1 mg-200 mg of forskolin and preferably, about 15 mg-100 mg.

Black tea extract for use in the present composition may be obtained from any suitable black tea leaf or black tea source including unblended black tea sources such as Congou, Assam, Darjeeling, Nilgiri or Ceylon or blended black teas such as Earl Grey, English Breakfast tea, English afternoon tea, Irish breakfast tea or Masala chai, which are derived from the *Camilla sinensis* leaf. Black tea is abundant in polyphenols such as theaflavins, thearubigins and catechins. Examples of theaflavins include theaflavin, theaflavin-3-gallate, theaflavin-3'-gallate and theaflavin-3,3'-gallate. Preferably, the black tea extract for use in the present composition comprises 10% or more of polyphenols by dry weight. Black tea extract for use in the present composition may be either caffeinated or substantially decaffeinated, for example, having less than 1% of caffeine by dry weight. Preferably, the black tea extract comprises at least about 30% polyphenols by dry weight. In one embodiment, the black tea extract comprises about 0.1-80% of the dry weight of the weight management composition, such as about 5-50%, or about 10-30% of the dry weight of the composition. In another embodiment, the weight management composition comprises a daily dosage of about 10 mg-5 g of black tea extract and preferably, about 50-750 mg.

Conjugated linoleic acid for use in the present application may be obtained from any suitable source such as safflower oil, sunflower oil or grass-fed beef sources. As used herein, the term "conjugated linoleic acid" refers to any of the at least 28 known geometric or positional isomers of linoleic acid, wherein two of the double bonds of the molecule are conjugated such as in the cis-9:trans-11 or trans-10:cis-12 form. The composition may include a single isomer, a mixture of isomers, natural isomers, synthetic isomers, or a pharmaceutically acceptable salt, ester, monoglyceride, diglyceride, triglyceride, metabolic precursor thereof, or any combinations thereof. Preferably, the conjugated linoleic acid contains about a 50:50 mixture of its cis-9:trans-11, and trans-10:cis-12 isomers. In one embodiment, the conjugated linoleic acid source comprises about 1%-80% of the dry weight of the weight management composition, such as about 20-70%, or about 30-50% of the dry weight of the composition. In another embodiment, the weight management composition comprises a daily dosage of about 10 mg-10 g of conjugated linoleic acid and preferably, about 500 mg-3 g.

The weight management composition comprises at least one mitochondria-enhancing agent. The mitochondria enhancing agent may be selected from any suitable agent which enhances mitochondrial capacity in a mammal, for example, by increasing the abundance of mitochondria, increasing the ATP generating capacity of mitochondria, protecting mitochondria from excessive oxidative stress, promoting the maintenance of mitochondrial components, ion gradients and ultrastructure, such as through increased mitochondrial autophagy (mitophagy) events or increased mitochondrial fission and fusion events.

In one embodiment, the mitochondria enhancing agent is selected from at least one of the following: beetroot extract, nitrates, idebenone, nicotinamide riboside, elamepratide, vitamin C, vitamin D, vitamin E, thiamine, riboflavin, magnesium, calcium, phosphate, membrane phospholipids, creatine, pyruvate, coenzyme Q10, NADH, nicotinic acid, l-carnitine, dichloroacetate, curcumin, schisandrin, resveratrol and mixtures thereof.

In one embodiment, the mitochondria enhancing agent comprises a mixture of beetroot extract, coenzyme Q10, alpha lipoic acid and vitamin E.

In another embodiment, the mitochondria enhancing agent comprises a mixture of beetroot extract, coenzyme Q10, alpha lipoic acid, creatine and vitamin E.

The beetroot extract for use in the present composition may be selected from any suitable beetroot source including red beets such as Detroit Dark Red, Red Ace. Early Wonder Tall Top, Bull's Blood, Forono, Ruby Queen, Chioggia, Cylindra or Gladiator, yellow or gold beets such as Yellow Detroit, Golden, Touchstone Gold or Boldor or white beets such as Avalanche, Baby White, Blankoma or Sugar. Preferably, the beetroot extract is substantially derived from the taproot portion of the beetroot. In one embodiment, the beetroot extract for use in the present composition comprises at least about 1.5% nitrates by dry weight. In another embodiment, the beetroot extract comprises about 0.1-90% of the dry weight of the weight management composition, such as about 1-50%, or about 5-25% of the dry weight of the composition. In a further embodiment, the weight management composition comprises a daily dosage of about 10 mg-50 g of beetroot extract and preferably, about 50-5000 mg.

Coenzyme Q10, also known as ubiquinone, ubidecarenone, coenzyme Q, CoQ10, CoQ, or Q10, may assume any one of three redox states for use in the present composition, namely, fully oxidized (ubiquinone), semi-oxidized (semiquinone or ubisemiquinone), and fully reduced (ubiquinol) forms, along with oxidized mitochondrially targeted forms of this enzyme (e.g. mitoquidone mesylate (MitoQ10)). As would be appreciated by one of skill in the art, coenzyme Q10 may be formulated in numerous ways to improve its bioavailability or effectiveness. Examples of such formulations for use in the present composition, which are not intended to be limiting, include the following: colloidal-based, solid dispersion-based, oily dispersion-based, micelle-based, nanoliposome-based, nanostructured lipid carrier-based, nanocrystal-based, nanoparticle-based, self-nanoemulsifiable-based, ascorbic acid with chelation-based and cyclodextrin complexation-based. In one embodiment, coenzyme Q10 comprises about 0.1-80% of the dry weight of the weight management composition, such as about 1-50%, or about 5-20% of the dry weight of the composition. In a further embodiment, the weight management composition comprises a daily dosage of about 10 mg-1 g of coenzyme Q10 and preferably, about 50-900 mg.

Alpha lipoic acid suitable for use in the present composition may include, without limitation, alpha lipoic acid or its reduced form, dihydrolipoic acid, with R- and S-enantiomers either present individually, in racemic form or in any other mixture thereof. The R-enantiomer is produced naturally or synthetically, while the S-enantiomer is only produced synthetically and does not occur naturally. Additionally, any pharmaceutically acceptable salts or derivatives thereof are suitable for use in the present composition. Preferably, the alpha lipoic acid is present in racemic form. In one embodiment, the alpha lipoic acid comprises about 0.1-90% of the dry weight of the weight management composition, such as about 5-50%, or about 10-30% of the dry weight of the composition. In another embodiment, the weight management composition comprises a daily dosage of about 10 mg-10 g of alpha lipoic acid and preferably, about 50 mg-900 mg.

Creatine for use in the present composition may be in any suitable form, such as creatine monohydrate, creatine anhydrous, creatine citrate, creatine ascorbate, creatine ethyl ester, creatine nitrate, creatine magnesium chelate, creatine hydrochloride, creatine malate, creatine pyruvate, creatine phosphate, creatine citrate malate, creatine tartrate, creatine HMB (β-hydroxy β-methylbutyrate), effervescent creatine, creatine titrate, buffered creatine, micronized creatine and any combination thereof. Preferably, the creatine is creatine monohydrate. In one embodiment, creatine comprises about 1%-90% of the dry weight of the weight management composition, such as about 20-70%, or about 30-50% of the dry weight of the composition. In another embodiment, the weight management composition comprises a daily dosage of about 0.1-10 g of creatine and preferably, about 0.5-5 g.

Vitamin E for use in the present composition may be in the form of any one or more of the isomers thereof, including alpha-tocopherol, beta-tocopherol, gamma-tocopherol, delta-tocopherol, alpha-tocotrienol, beta-tocotrienol, gamma-tocotrienol, and delta-tocotrienol, and stereoisomers thereof. Vitamin E may also be used in analogue form, including, for example, vitamin E esters (such as acetate, succinate or palmitate forms) or other forms of vitamin E which have been modified for improved stability or bioavailability. Preferably, the form of vitamin E used in the composition is alpha-tocopherol comprising biologically functional stereoisomers of alpha-tocopherol such as the naturally occurring RRR-configuration or the synthetically produced 2R-stereoisomer forms (RSR-, RRS-, and RSS-). In the most preferred embodiment, the vitamin E used is D (also known as RRR)-alpha tocopheryl acetate. In one embodiment, the vitamin E comprises about 0.1-80% of the dry weight of the weight management composition, such as about 1-50%, or about 3-15% of the dry weight of the composition. In a further embodiment, the weight management composition comprises a daily dosage of about 10 mg-1 g of vitamin E and preferably, about 50-900 mg.

In one embodiment, the weight management composition comprises as the weight loss agent a mixture comprising a daily dosage of 50-1000 mg of green tea extract, 50-1000 mg of green coffee bean extract, 15-100 mg of forskolin, and as the mitochondria enhancing agent a mixture comprising a daily dosage of 50-5000 mg of beetroot extract, 50-900 mg of coenzyme Q10, 50-900 mg alpha lipoic acid and 50-900 mg of vitamin E.

In another embodiment, the weight management composition comprises as the weight loss agent a mixture comprising a daily dosage of 50-500 mg of green tea extract, 50-500 mg of black tea extract, 50-500 mg of green coffee bean extract, 500 mg-3 g of conjugated linoleic acid and 15 mg-50 mg of forskolin, and as the mitochondria enhancing agent a mixture comprising a daily dosage of 100-1000 mg of beetroot extract, 50-200 mg of coenzyme Q10, 50 mg-500 mg alpha lipoic acid, 1-5 g of creatine and 50-200 mg or vitamin E.

In one embodiment, caffeine is present in the weight management composition either as anhydrous caffeine or within a naturally occurring source such as green tea or green coffee beans. The anhydrous caffeine may be derived from any suitable source, such as from any one of about 60 plant species naturally containing caffeine, which include tea leaves, coffee beans, cocoa beans, yerba maté, guarana berries, guayusa, and the yaupon holly. Preferably, the weight management composition comprises a daily dose of approximately 25-1000 mg of caffeine, such as about 100-250 mg.

In another embodiment, the weight management composition is substantially caffeine free. In the substantially caffeine free weight management composition, ingredients which naturally contain caffeine may be provided in decaffeinated form, such that each decaffeinated ingredient contains less than 1% of caffeine by dry weight for example. Methods for decaffeination are known in the art.

According to one embodiment, the weight management composition may be used as a sole, primary, or supplemental source of nutrition. Where the weight management composition is used as a sole source of nutrition, the composition will generally comprise other essential nutrients required in an adequate diet, such as vitamins, minerals, proteins, carbohydrates, fibre, and fats/lipids as would be appreciated by one of skill in the art.

Where the weight management composition is used as other than a sole source of nutrition, it may be formulated with at least one additional source of nutrition, including, but not limited to; proteins, carbohydrates, lipids, fibre, vitamins, minerals, antioxidants, prebiotics, probiotics, phytochemicals or phytonutrients.

Proteins suitable for inclusion in the weight management composition include any food-grade protein which is suitable for oral administration to an individual. Proteins may be selected from any suitable protein source, including those from an animal source, a dairy source, a plant source, an insect source or any combination thereof. Non-limiting examples of insect sources of protein include: cricket protein, grasshopper protein, mealworm protein, earthworm protein and any combination thereof. Non-limiting examples of animal sources of protein include: cow protein, pig protein, goat protein, lamb protein, poultry protein (such as chicken, duck, goose, pheasant and the like), wild game protein, seafood protein (such as fish and shellfish) and any combination thereof. Non-limiting examples of dairy sources of protein include: whey protein, whey protein concentrate, whey protein isolate, milk protein concentrate, milk protein isolate, powdered fat and/or fat-free milk, micellar casein, acid casein, potassium caseinate, calcium caseinate, sodium caseinate and any combination thereof. Non-limiting examples of plant sources of protein include: pea protein, yeast protein, soy protein, corn protein, wheat protein, rice protein, canola protein, peanut protein, bean protein, lentil protein, and any combination thereof. The protein source may be non-hydrolyzed, partially hydrolyzed or hydrolyzed and may be in the form of an intact protein, amino acid or peptide. Non-limiting examples of amino acids may include essential amino acids such as: leucine, isoleucine, valine, tryptophan, methionine, threonine, phenylalanine and lysine and semi-essential amino acids such as: histidine and arginine and non-essential amino acids such as tyrosine, aspartic acid, glycine, alanine, cysteine, arginine, glutamic acid, proline, glutamine, serine, asparagine, taurine and any combination thereof. Preferably, the protein source is a high-quality protein source, at least comprising each of the essential amino acids. More preferably, the protein source is a high-quality protein source containing an additional amount of leucine. In one embodiment, the present composition may include about 0.1-99% by wt protein.

Carbohydrates suitable for inclusion in the weight management composition include any food-grade carbohydrate which is suitable for oral administration to an individual. Suitable carbohydrates include the following non-limiting examples: quickly-digestible carbohydrates such as monosaccharides, disaccharides or polysaccharides (e.g. glucose, fructose, sucrose, dextrose, maltodextrin and maltose), molasses, honey, maple syrup, corn syrup, high fructose corn syrup, sugar alcohols (e.g. xylitol, maltitol, erythritol, sorbitol, hydrogenated starch hydrolysates, isomalt and mannitol) or more slowly-digestible carbohydrates such as katakuri starch, cornstarch, potato starch, arrowroot, alginin, xanthan gum, locust bean gum, oat bran, wheat bran and rice bran, or combinations thereof. In one embodiment, the present composition may include about 0.1-99% by wt carbohydrates.

The weight management composition may comprise any food-grade source of fibre which is suitable for oral administration to an individual. Suitable sources of fibre include the following non-limiting examples: water-soluble dietary fiber such as beta-glucans, pectin, xylose, plant gums, inulin and alginates, and insoluble dietary fiber such as lignin, beta-glucans, xanthan gum, resistant starches and combinations thereof. Fibre may be included in the composition in an amount that does not adversely affect the function of the composition.

The weight management composition may comprise any food-grade source of lipids suitable for oral administration to an individual. Suitable sources of lipids include the following non-limiting examples: olive oil, safflower oil, canola oil, coconut oil, corn oil, palm oil, palm kernel oil, soybean oil, peanut oil, fish oil, almond oil, sunflower oil, butter, lard, and sources of medium chain triglycerides, long chain triglycerides, monoglycerides, diglycerides, cold water fish (e.g. cod, salmon, tuna, sardines, mackerel, krill and squid), algae, dark leafy green vegetables, plant and plant seed oils (e.g. flaxseed oil, canola oil and walnut oil), nuts (e.g. walnuts) and combinations thereof. Lipids may be included in the composition in an amount that does not adversely affect the function of the composition.

The weight management composition may comprise any food-grade source of vitamins and minerals which are suitable for oral administration to an individual. Suitable vitamins include the following non-limiting examples: vitamin A, vitamin C, vitamin D, vitamin K, thiamine, riboflavin, niacin, pantothenic acid, pyridoxine, folic acid, cobalamin, biotin, carotenoids (e.g. lutein, beta-carotene, lycopene and cryptoxanthin), choline, inositol and combinations thereof, and suitable minerals include, but are not limited to, calcium, phosphorus, selenium, chromium, zinc, molybdenum, iodine, chloride, phosphorus, manganese, fluoride, potassium, iron, copper, magnesium, sodium and combinations thereof. Vitamins may be included in an amount that complies with recommended daily dosages, either alone or in combination with diet. Vitamins and minerals may be included in the composition in an amount that does not adversely affect the function of the composition.

The weight management composition may comprise any food-grade source of antioxidants which are suitable for oral administration to an individual. Suitable antioxidants include the following non-limiting examples: citric acid monohydrate, vitamin A, vitamin C, folic acid, and beta-carotene, iron, copper, butylated hydroxyamisole, butylated hydroxytoluene, propyl gallate, tertiary butylhydroquinone, resveratrol, and plant phytonutrients or phytochemicals (e.g. flavonoids and lignin). Herbs or herbal extracts (e.g. oregano, Goji berry, dill, garden thyme, rosemary and peppermint), tea leaves or tea leaf extracts (e.g. *Camellia sinensis*), coffee bean extracts (e.g. *Coffea canephora* and *Coffea arabica*), brewed coffee or tea or brewed coffee or tea extracts (e.g. oolong tea and *Coffea robusta*) and other plants or plant extracts (e.g. ginger root) may also be used as a source of antioxidants, as well as combinations of any of the antioxidants. Antioxidants may be included in the composition in an amount that does not adversely affect the function of the composition.

The weight management composition may comprise any food-grade source of prebiotics which are suitable for oral administration to an individual. Suitable prebiotics include the following non-limiting examples: dietary fibers and carbohydrate polymers such as cellulose, inulin, gums, trans-galactooligosaccharide, fructans, resistant starches, xylooligosaccharides, hemicelluloses, pectin, sugar alcohols, beta-glucans and combinations thereof.

The weight management composition may comprise any food-grade source of probiotics which are suitable for oral administration to an individual. Suitable probiotics include the following non-limiting examples: *Lactobacillus Acidophilus, Lactobacillus Reuteri, Lactobacillus Rhamnosus,*

*Lactobacillus Gasseri, Lactobacillus Salivarius, Lactobacillus Bulgaricus, Lactobacillus Helventicus, Lactobacillus Silivarus, Lactobacillus Plantarum, Lactobacillus Casei, Lactobacillus Paracassei, Lactobacillus Fermenium, Bifidobacterium Breve, Bifidobacterium Lactis, Bifidobacterium Longum, Bifidobacterium Bifidum, Bifidobacterium Infantis, Bifidobacterium Bifidum, Bacillus Coagulans, Saccharomyces Boulardii, Pediococcus Acidlacti* and combinations thereof.

The weight management composition may comprise any food-grade source of phytochemicals or phytonutrients which are suitable for oral administration to an individual. Suitable phytochemicals or phytonutrients include the following non-limiting examples: phytosterols including sterols (e.g. cempesterol) and stanol (e.g. sitostanol), soy flavonoids (e.g. genistein and glycitein), garlic and organosulfur compounds (e.g. L-cysteine sulfoxides and γ-glutamyl-L-cysteine peptides), carotenoids (e.g. zeaxanthin alpha-carotene, beta-carotene, lycopene, beta-cryptoxanthin and lutein), resveratrol, curcumin, fiber (e.g. lignin and cellulose), indole 3-carbinol and condensation products (e.g. 3,3'-diindolylmethane and 5,11-dihydroindolo-[3,2-b]carbazole), chlorophyll and chlorophyllin isothiocyanates, isothiocyanates (e.g. sulforaphane and benzyl isothiocyanate) and combinations thereof.

Prebiotics, probiotics, phytochemicals and phytonutrients may be included in the composition in an amount that does not adversely affect the function of the composition.

The present composition may additionally include at least one physiologically acceptable excipient. The term "physiologically acceptable" is used herein to refer to excipients which are food-grade and thus, acceptable for consumption or administration to a mammal. Examples of suitable excipients, which are not to be construed as limiting, include flavouring agents, sweetening agents, anti-caking agents/flowing agents, emulsifiers, stabilizers, masking agents, colorants, preservatives, disintegrants, binders, thickeners and pH adjusters.

Non-limiting examples of flavouring agents include natural or artificial flavours such as fruit flavours (e.g. raspberry, orange, apple, pomegranate, mixed berry, lemon, lime, watermelon, strawberry, blueberry, pineapple, coconut, grape, cherry, banana, peach, mango, kiwifruit, cranberry), sodium sources (e.g. sodium chloride and monosodium glutamate), high fructose corn syrup, vanilla, chocolate, unsweetened chocolate, honey, molasses, brown sugar, coffee, cocoa, mint, maple, almond, or extracts or combinations thereof. Savoury flavourings may also be used (e.g. beef, chicken or vegetable flavourings).

Non-limiting examples of sweetening agents include natural sweeteners such as, glucose, fructose, sucrose, dextrose, maltose, brown sugar, molasses, honey, maple syrup, corn syrup, high fructose corn syrup, erythritol, xylitol, sorbitol, isomalt, monatin, monellin, curculin, brazzein, tagatose and mannitol, and artificial sweeteners such as aspartame, acesulfame K, saccharin cyclamate and sucralose.

Non-limiting examples of further excipients include: anti-caking agents or flowing agents such as silicates (e.g. silicon dioxide) and calcium or magnesium stearates; emulsifiers such as agar, gums, egg yolk, lecithin, monostearate, monosodium phosphate, monoglycerides, diglycerides and alginates; stabilizers such as glycerine, agar, gums, alginates and pectin; masking agents such as glycerine, sodium chloride, peppermint, lemon-lime, mint, cherry, black liquorice, peach, apricot, raspberry, or sweetening agents such as aspartame or sucrose; colorants such as those which are suitable for inclusion in foods, e.g. FD&C blue #1, FD&C blue #2, FD&C citrus red #2, FD&C green #3, FD&C red #3, FD&C red #40, FD&C yellow #5 and FD&C yellow #6; preservatives such as butylated hydroxyanisole, butylated hydroxytoluene, ethylenediaminetetraacetic acid, nitrates (e.g. sodium nitrate), sulfites (sodium bisulfite), benzoates (sodium benzoate), sorbates (e.g. sodium sorbate) and sodium chloride; disintegrants such as starches (e.g. potato starch), alginic acid, cellulose and derivatives thereof, and calcium silicate; binders such as stearic acid, gelatin, saccharides and derivatives thereof, sugar alcohols, polyethylene glycol and cellulose; thickeners such as polysaccharide-based thickeners such as vegetable gums, pectin and starches or protein-based thickeners such as gelatin, egg white and collagen; and pH adjusters such as citric acid, ammonium carbonate, ammonium phosphate, calcium carbonate, sodium hydroxide, malic acid and phosphoric acid. As will be appreciated by one of skill in the art, for each type of excipient (e.g. flavouring agent, sweetener, emulsifier, preservative, etc.), a single excipient may be used, or a combination of two or more may be used.

The weight management composition may be formulated for oral administration including, for example, solid, semi-solid, liquid, semi-liquid, powder, suspension, emulsion, solution, ready-to-drink beverage, gel, bar, pill, tablet or capsule form. The term "oral" or "orally" as used herein is intended to include any method in which the weight management composition is introduced into the digestive tract including the stomach and small intestine. Examples of oral administration may include administration via mouth, directly into the stomach using a feeding tube, through the nose to the stomach via a feeding tube and through the nose to the small intestine via a feeding tube. In a preferred embodiment, the weight management composition is provided as a loose powder, a bar or in capsules. The loose powdered composition may be reconstituted in water or any suitable liquid (such as juice, milk, saline, etc.) immediately prior to consumption. When provided in loose powdered form, the weight management composition may be packaged in individual use containers, packets or sachets, or in larger bulk containers. When provided as a powder in capsules, any suitable capsule may be used including gelatin and hard hydroxypropyl methylcellulose (also known as Hypromellose) capsules.

The weight management composition may also be administered parenterally, either alone or in combination with at least one pharmaceutically acceptable adjuvant, for use in methods in accordance with embodiments of the invention. The expression "pharmaceutically acceptable" means acceptable for use in the pharmaceutical and veterinary arts, i.e. not being unacceptably toxic or otherwise unsuitable. Examples of pharmaceutically acceptable adjuvants include diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the composition is formulated for administration by infusion, or by injection either subcutaneously or intravenously. The composition may be prepared as an aqueous solution in sterile and pyrogen-free form and optionally buffered or made isotonic. Thus, the composition may be administered in distilled water or, more desirably, in saline, phosphate-buffered saline or 5% dextrose solution. Creams, lotions and ointments may be prepared for topical application using an appropriate base such as a triglyceride base. Such creams, lotions and ointments may also contain a surface active agent. Aerosol formulations may also be prepared in which suitable propellant adjuvants are used. Other adjuvants may also be added to the composition regardless of how it is to be administered for example, anti-microbial agents may be added to the composition to prevent microbial growth over prolonged storage periods. The composition may include a coating or may be encased in a protective material to prevent undesirable degradation thereof by enzymes, acids or by other conditions that may affect the therapeutic activity thereof.

The weight management composition may be administered in a daily effective amount to a mammal in need thereof, one or more times per day, for a period ranging from one day to chronic or long-term administration. The term "mammal" is used herein to refer to human and non-human mammals such as domestic animals (cats, dogs, horses and other livestock). The term "daily effective amount" as used herein, refers to an amount which achieves the effects desired in the mammal, without surpassing any amount which may cause undesirable side effects. For example, a daily effective amount of the weight management composition may be administered once per day, or a daily effective amount of the weight management composition may be divided into 2, 3, 4, 5, 6 or more portions to be administered throughout the day. In one embodiment, the weight management composition is administered once a day to an individual in the morning when first waking up. The weight management composition may be administered to an individual in need thereof for 1, 2, 3, 4, 5, 6 or 7 days in a week and for 1, 2, 3, 4, 5, 6, 7, 8, 9, 10 or more weeks. In one embodiment, the weight management composition is administered chronically to an individual in need thereof. The term "chronically" as used herein refers to the administration of the weight management composition for a period of at least 2-4 or more months, for example, administration of the weight management composition on a continual basis beyond 6 months, at a frequency of at least 2 days/week, and preferably at least 3 or more days a week. In one embodiment, the daily effective amount of the weight management composition is consumed over two servings, with one serving being administered in the morning and the remaining serving being administered in the afternoon or evening for a period of 3 months. In another embodiment, the daily effective amount of the weight management composition is consumed over three servings, with one serving being administered in the morning, the second serving being administered around midday and the third serving being administered in the evening for a period of 3 months.

The components of the composition may be administered in conjunction, either together, in a single composition, or individually in separate dosage forms which may be the same or different, and which may be administered at the same time or at different times. For example, the weight loss agent may be administered in tablet form, while the mitochondrial enhancing agent may be administered separately in a different administrable dosage form, such as a capsule. The mitochondrial agent may be administered at the same time as the weight loss agent is administered, or at a different time, and at the same frequency or at a different frequency. For example, the weight loss tablet may be administered twice daily, while the mitochondrial enhancing capsules are administered once or twice a day. In one embodiment, each of the weight management composition components are provided in capsule form, together or separately, with the exception of creatine, which is provided in tablet form.

The present weight management composition is useful in a method to treat or improve at least one of the following in a mammal: body weight, body fat, mitochondrial capacity, fatty liver disease, dyslipidemia, oxidative stress levels, BAT activity and systemic inflammation levels. The term "individual" is used herein to refer to a mammal, preferably a human. The method comprises administering to the individual an effective amount of the weight management composition. Any individual may be treated using the present method, including individuals of any age. The terms "treat", "treating" or "treatment" are used herein to refer to methods that favourably alter body weight, body fat, liver intra-cytosolic lipid deposits, blood lipid levels, oxidative stress levels, BAT activity, systemic inflammation levels and mitochondrial energy generating capacity, including those that moderate, reverse, reduce the severity of, or protect against, the progression of conditions associated with the dysregulation of body weight, body fat, liver intra-cytosolic lipid deposits, blood lipid levels, oxidative stress levels, BAT activity, systemic inflammation levels and mitochondrial energy generating capacity. The term "improve" is used herein with respect to the variables of body weight, body fat, liver intra-cytosolic lipid deposits, blood lipid levels, oxidative stress levels, BAT activity, systemic inflammation levels and mitochondrial energy generating capacity refer to either a healthy increase or a healthy decrease in the variable, i.e. an increase or decrease in the variable, whichever is considered to promote health. For example, generally the treatment will achieve at least one of weight loss, an increase in mitochondrial capacity, a decrease in liver intra-cytosolic lipid deposits to treat fatty liver disease, a decrease in blood lipid levels to treat dyslipidemia, a decrease in oxidative stress levels, an increase in BAT activity and a decrease in systemic inflammation levels.

The present method is useful for healthy individuals, as well as individuals that require treatment of one or more of body weight, body fat, fatty liver disease, dyslipidemia, oxidative stress levels, BAT activity, systemic inflammation levels and mitochondrial capacity, for example, elderly individuals, bed-ridden individuals, hospitalized individuals and individuals afflicted with a disease or condition that adversely effects one or more of body weight, body fat, fatty liver disease, dyslipidemia, oxidative stress levels, BAT activity, systemic inflammation levels and mitochondrial capacity.

As used herein, the term "body weight" refers to the total body mass of an individual or to the mass of specific regions of the body. Improved body weight is a reduction of body weight in an individual by at least about 0.5%, and preferably a reduction of about 1% or more, e.g. by 5%, 10%, 30%, 50%, 70% or greater of body weight in the individual prior to treatment with the present composition or a reduction in the rate of rising body weight by at least about 1% or more, and preferably a reduction of about 5% or more, e.g. by 10%, 30%, 50%, 70%, 90% or greater to the rate of body weight increase prior to treatment. With respect to body weight, the present composition surprisingly exhibits a synergistic effect, i.e. the effect of the combination of a weight loss agent and a mitochondrial enhancing agent results in a reduction of body weight that is greater than the additive effect of a weight loss agent alone, and a mitochondrial enhancing agent alone. This in turn will be reflected in other treatments for which the composition is useful insofar as an improvement in body weight and reduction in body fat promotes such treatments.

As used herein, the term "body fat" refers to the total fat mass of an individual or to the fat mass of specific regions of the body. During healthy weight loss, the majority of body weight loss is derived from the reduction of excess fat stores in an individual. Improved body fat is a reduction of body fat in an individual by at least about 0.5%, and preferably a reduction of about 1% or more, e.g. by 5%, 10%, 30%, 50%, 70% or greater of body fat in the individual prior to treatment with the present composition, or a reduction in the rate of rising body fat by at least about 1% or more, and preferably a reduction of about 5% or more, e.g. by 10%, 30%, 50%, 70%, 90% or greater to the rate of body fat increase prior to treatment.

As used herein, the term "mitochondrial capacity" refers to the total physiological productive capacity for mitochondria to produce cellular energy stores by carrying out cellular respiration. The term encompasses the mitochondrial capacity of one or more mitochondria and may be used to refer to the mitochondrial capacity of mitochondria within specific regions (such as specific muscles or organs) or within the entire body. Important indicators of mitochondrial capacity include the following non-limiting examples: an increase in the mRNA expression of mitochondrial capacity biomarkers such as PGC1 alpha, COX2, PPAR alpha, HSL, SCHAD, UCP3, PRDM16, CIDEA and AIPOQ, an increase in the total number of mitochondria (also known as mitochondrial volume density) in a tissue, an increase in the enzymatic capacity expressed in absolute terms or relative to the total number of mitochondria measured, the presence of biomarkers of mitochondrial integrity, such as the absence of deletions, cristae fragmentation or pleomorphism and a heightened amount (but not an excessive amount) of mitochondrial turnover via mitophagy or mitochondrial fission and fusion events. For example, improved mitochondrial capacity refers to an increase in the mRNA expression of mitochondrial capacity biomarkers in an individual by at least about 0.5%, and preferably an increase of about 1% or more, e.g. by 5%, 10%, 30%, 50%, 70% or greater from the mRNA expression of mitochondrial capacity biomarkers of the individual prior to treatment with the present composition, or at least a reduction in the rate of mRNA expression of mitochondrial capacity biomarker decline in an individual who is experiencing a decrease in the mRNA expression of mitochondrial capacity biomarkers by at least about 1% or more, and preferably a reduction in the rate of mitochondrial capacity loss by about 5% or more, e.g. by 10%, 30%, 50%, 70%, 90% or greater from the rate of mRNA expression of mitochondrial capacity biomarker decline in the individual prior to treatment with the present composition. Improved mitochondrial capacity may also refer to a normalization of mitochondrial capacity in one or more tissues within the levels of a healthy individual.

As used herein, the term "fatty liver disease" is intended to encompass a spectrum of metabolic fatty liver diseases, which progress in severity from fatty liver (also known as steatosis) to steatohepatitis to fibrosis/cirrhosis and potentially liver failure or hepatocellular carcinoma. Fatty liver disease is also intended to refer to both the nonalcoholic fatty liver disease and alcoholic liver disease (ALD). Indicators of the presence or development of fatty liver disease may include liver triglyceride accumulation, liver inflammation biomarkers, liver endoplasmic reticulum stress biomarkers, liver hepatocellular injury or hepatocyte death biomarkers and liver fibrosis biomarkers. For example, improved fatty liver disease is a reduction of liver intra-cytosolic lipid deposits in an individual by at least about 0.5%, and preferably a reduction of about 1% or more, e.g. by 5%, 10%, 30%, 50%, 70% or greater of liver intra-cytosolic lipid deposits in the individual prior to treatment with the present composition, or a reduction in the rate of rising liver intra-cytosolic lipid deposits by at least about 1% or more, and preferably a reduction of about 5% or more, e.g. by 10%, 30%, 50%, 70%, 90% or greater to the rate of liver intra-cytosolic lipid deposit increase prior to treatment.

As used herein, the term "dyslipidemia" refers to an abnormal level of lipids in the blood, and the term commonly refers to elevated blood levels of non-HDL cholesterol (which includes chylomicrons, LDL cholesterol, IDL cholesterol and VLDL cholesterol), triglycerides or low levels of blood HDL cholesterol. Reducing the amount of total blood non-HDL cholesterol, or increasing HDL cholesterol generally leads to a reduced risk of, or slows the progression of atherogenic changes that may lead to coronary artery disease. One of the most accurate ways to diagnose elevated blood cholesterol is to measure the ApoB protein as this biomarker represents the non-HDL proteins in the blood, while ApoA1 is often used as a biomarker of blood HDL levels. Furthermore, an elevated ratio of ApoB/ApoA1 has been shown to act as a clinically significant biomarker of cardiovascular disease in overweight or obese individuals. For example, improved dyslipidemia is a reduction of blood non-HDL lipids in an individual by at least about 0.5%, and preferably a reduction of about 1% or more, e.g. by 5%, 10%, 30%, 50%, 70% or greater of blood non-HDL lipids in the individual prior to treatment with the present composition, or a reduction in the rate of rising blood non-HDL lipids by at least about 1% or more, and preferably a reduction of about 5% or more, e.g. by 10%, 30%, 50%, 70%, 90% or greater to the rate of blood non-HDL lipid increase prior to treatment. Improved dyslipidemia may also refer to an increase in the amount of blood HDL cholesterol in an individual by at least about 0.5%, and preferably an increase of about 1% or more, e.g. by 5%, 10%, 30%, 50%, 70% or greater from the blood H-IDL cholesterol level of the individual prior to treatment with the present composition, or at least a reduction in the rate of blood HDL cholesterol level decline in an individual who is experiencing a decline of blood HDL cholesterol level by at least about 1% or more, and preferably a reduction in the rate of blood HDL cholesterol level decline by about 5% or more, e.g. by 10%, 30%, 50%, 70%, 90% or greater from the rate of blood HDL cholesterol level decline in the individual prior to treatment with the present composition.

As used herein, the term "oxidative stress" refers to the amount of free radical or free radical producing agents present in circulation and within tissues of the body. Oxidative stress is known to induce modifications which alter the functioning of proteins, lipids, DNA and other cellular components. Chronically elevated oxidative stress has been associated with and shown to exacerbate the development of obesity and obesity-associated co-morbidities such as insulin resistance, dyslipidemia, heart disease and fatty liver disease for example. Oxidative stress level is most commonly evaluated by measuring the biomarkers of oxidatively modified cellular products such as protein carbonyls and peroxidized lipids (trans-4-hydroxy-2-nonenal (4-HNE) for example). For example, improved oxidative stress level is a reduction in 4-HNE protein levels in an individual by at least about 0.5%, and preferably a reduction of about 1% or more, e.g. by 5%, 10%, 30%, 50%, 70% or greater to the level of 4-HNE protein levels prior to treatment with the present composition, or at least a reduction in the rate of increase of 4-HNE protein levels by at least about 1% or more, and preferably a reduction of the rate of increase of 4-HNE protein levels by about 5% or more, e.g. by 10%, 30%, 50%;

70%, 90% or greater to the rate of increase of 4-HNE protein levels prior to treatment with the present composition.

As used herein, the term "BAT activity" refers to the total thermogenic activity of brown or beige adipocytes in an individual or to the thermogenic activity of brown or beige adipocytes in any one or more regions (such as one or more brown or beige adipocytes in an adipose tissue depot). Brown or beige adipose tissue is known to promote energy expenditure by increasing oxidative phosphorylation that is uncoupled from ATP generation, causing energy release in the form of heat. Beige adipocytes are commonly understood to be white adipocytes that have undergone transdifferentiation to exhibit an increase in "brown-like" characteristics, such as having a higher mitochondrial density and capacity for mitochondrial uncoupling. Three of the common methods of improving BAT activity include the following: 1) converting one or more of the white adipocytes in an individual into beige adipocytes, 2) newly forming beige adipocytes from adipogenic progenitor cells, and 3) increasing the thermogenic activity of existing brown adipocytes. Activation of BAT is most commonly evaluated by measuring the mRNA expression or protein levels of BAT biomarkers such as UCP3, PRDM16, CIDEA, PPAR alpha and PGC1 alpha. For example, improved BAT activity refers to an increase in the amount of mRNA expression of BAT biomarkers in an individual by at least about 0.5%, and preferably an increase of about 1% or more, e.g. by 5%, 10%, 30%, 50%, 70% or greater from the mRNA expression of BAT biomarkers of the individual prior to treatment with the present composition, or at least a reduction in the rate of mRNA expression of BAT biomarkers decline in an individual who is experiencing a decrease of mRNA expression of BAT biomarkers by at least about 1% or more, and preferably a reduction in the rate of mRNA expression of BAT biomarkers decline by about 5% or more, e.g. by 10%, 30%, 50%, 70%, 90% or greater from the rate of mRNA expression of BAT biomarkers decline in the individual prior to treatment with the present composition.

As used herein, the term "systemic inflammation level" refers to the amount of inflammation present in circulation and within tissues of the body. While acute inflammation in response to injurious events is thought to be beneficial, the presence of a chronic-low grade inflammation level is generally thought to be deleterious and likely related to the development of other chronic diseases associated with obesity. Systemic inflammation level is most commonly evaluated by measuring the mRNA expression or protein levels of pro-inflammatory biomarkers such as C-reactive protein (CRP), interleukin-6 (IL-6), IL1 beta and tumor necrosis factor-alpha (TNF-alpha) in circulation. Other common biomarkers of systemic inflammation include pro-inflammatory cytokines such as IL-1B, IL-12 and IL-18, chemokines such as CXCL-8, CCL2, CCL3, CCL4, CCL5, CCL11 and CCXCL10 and growth factors such as GM-CSF, PDGF, TGF-Beta and VEGF. For example, improved systemic inflammation level is a reduction in the mRNA expression of inflammation biomarkers in an individual by at least about 0.5%, and preferably a reduction of about 1% or more, e.g. by 5%, 10%, 30%, 50%, 70% or greater to the mRNA expression of inflammation biomarkers prior to treatment with the present composition, or at least a reduction in the rate of an increase of mRNA expression of inflammation biomarkers by at least about 1% or more, and preferably a reduction of the rate of increase of mRNA expression of inflammation biomarkers by about 5% or more, e.g. by 10%, 30%, 50%, 70%, 90% or greater to the rate of mRNA expression of inflammation biomarkers prior to treatment with the present composition.

In another embodiment, the present weight management composition is useful in a method for treating obesity and may also treat one or more obesity associated co-morbidities in an individual, such as fatty liver disease (e.g. steatosis, steatohepatitis and cirrhosis), cardiovascular disease (e.g. coronary artery disease and arrhythmias), type 2 diabetes, hypertension, dyslipidemia (e.g. high LDL cholesterol, low HDL cholesterol, high triglycerides), gallbladder disease, osteoarthritis, sleep apnea, asthma, chronic kidney disease and depression. The method comprises administering to the individual a weight management composition comprising a weight loss agent and a mitochondria enhancing agent.

In another embodiment, the present methods of promoting weight management, reducing body weight and body fat and treating obesity in an individual, may advantageously comprise administration of the weight management composition to an individual who is also performing regular exercise.

The term "exercise" is meant to encompass endurance exercise, high-intensity interval training, resistance exercise, and the like, e.g. exercise that achieves a level of working of at least about 3-6 metabolic equivalents (METS), and combinations thereof (e.g. any combination of endurance exercise, high-intensity interval exercise, or >50% of the one repetition maximum (resistance exercise)). METS is the energy expenditure of a physical activity or exercise defined as the ratio of the metabolic rate of an exercising individual (and therefore the rate of energy consumption) during a specific physical activity to a reference basal metabolic rate. In a preferred embodiment, the exercise is performed on a regular basis. Regularly performing exercise refers to the performance of exercise for a duration of at least a month and preferably chronically such as for 2, 4 or 6 or more months, at a frequency of at least 2 days/week, and preferably at least 3 or more days a week, for a period of at least 30 consecutive minutes per day, preferably 45 minutes or greater, such as 60 minutes or greater, or 75-90 minutes or more. Exercise may include endurance activities such as brisk walking, jogging, running, dancing, swimming, bicycling, sports, interval training, resistance exercise, and the like. Interval training refers to repetitive bouts of exercise that may be at high or lower intensity provided it meets minimal METS requirements. High intensity interval training would include activities such as sprints (e.g. 10 second to 4 minute sprints) followed by a recovery time (e.g. of 10 seconds to 4 minutes). The term "resistance exercise" refers to weight training or other resistance exercise (plyometrics, hydraulic machines, etc.) with a resistance of at least 50% of the one repetition maximum, performed in sets of repetitions (for example, 8-15 repetitions), followed by a recovery between sets, for a period of time sufficient to achieve minimal METS requirements. One repetition maximum is the maximal voluntary contraction strength for a single movement where a second movement is impossible.

The weight management composition may be administered at any time relative to the performance of exercise, i.e. before, during or following the exercise, or any combination thereof. In one embodiment, the weight management composition is administered to an individual immediately following exercise.

Unless otherwise indicated, the definitions and embodiments described in this and other sections are intended to be applicable to all embodiments and aspects of the present application herein described for which they are suitable as would be understood by a person skilled in the art.

EXAMPLES

Example 1—Weight Management Composition Improves Body Weight, Fat Mass and Mitochondrial Capacity In Vivo To determine if a weight management composition, in accordance with an embodiment of the invention, comprising a weight loss agent and a mitochondria enhancing agent could: 1) reduce body weight and body fat, and improve mitochondrial capacity; and/or 2) enhance exercise-mediated improvements in body weight, body fat and mitochondrial capacity, high-fat diet (HFD) fed mice were administered the weight management composition or one of several control compositions and were either exercised or remained sedentary for a period of 30 days.

All experiments were approved by the McMaster University Animals Ethics Committee and conducted under appropriate Canadian guidelines for animal research. Sixty of C57/Bl6, diet-induced obesity mice were ordered from Jackson Laboratories, which were placed on a HFD (Teklad #TD.06414) containing 60% energy from fat at 6 weeks and fed ad libitum. At approximately 12 weeks of age, mice were allocated into experimental groups which where standardized by average body weight. Each of the experimental groups were fed one of the following HFDs containing 60% energy from fat: Group 1 were fed HFD control (referred to as HFD control; with energy density of 5.1 Kcal/g), Group 2 were fed HFD containing weight loss agents (referred to as WL only diet; with energy density of 5.1 Kcal/g and containing weight loss agents in the following amounts: 0.25% green tea extract, 0.13% black tea extract, 0.25% green coffee bean extract, 0.25% conjugated linoleic acid and 0.005% forskolin by weight), Group 3 were fed HFD containing mitochondria enhancing agents (referred to as ME only diet; with energy density of 5.0 Kcal/g and containing mitochondria enhancing agents in the following amounts: 1% beetroot juice extract, 0.25% coenzyme Q10, 0.1% alpha lipoic acid and 1% creatine by weight and an additional 1000 IU/kg of vitamin E) and Group 4 were fed HFD containing both weight loss agents and mitochondria enhancing agents (referred to as Weight management combination A diet; with energy density of 5.0 Kcal/g and containing weight loss agents in the same amounts as Group 2 and mitochondria enhancing agents in the same amounts as Group 3). 10 mice per group for Groups 1-4 were then individually housed in standard microisolator cages and fed their respective diets for 30 days. To evaluate the effects of the Weight management combination A diet on exercise, Group 5 consisted of another group of 10 mice which were fed the Weight management combination A diet, but were individually housed in cages containing an exercise wheel which allowed the mice to voluntarily exercise at will and were additionally exercised three times weekly on a treadmill at a speed of 15 m/min for 45 minutes. As a further control, Group 6 consisted of 10 mice which were fed the HFD control and subjected to the same housing and exercise regime as Group 5 in order to provide a reference to the effects of exercise alone on mice fed a HFD. Lastly, Group 7 consisted of 10 C57/Bl6 mice (Jackson laboratories, Cat. #000664), which were fed a standard mouse chow diet (referred to as Chow diet), with energy density of 3 Kcal/g; Envigo, diet #8640) from weeks 0-12, were housed in microisolator cages and continued on Chow diet for 30 days in order to serve as a third control, which demonstrates the effects of a healthy diet on body composition.

Beginning 7 days prior to the introduction of the experimental diets (i.e. day −7), baseline testing was conducted on all of the mice. Baseline testing included the following measurements: body weight, relative fat mass and lean body mass, grip strength, motor coordination and maximal running capacity. On day 0, the experimental diets were introduced to all mice and the two exercise groups were placed in the running wheel cages and began the treadmill exercise regime. Body weight was measured daily throughout the study and food intake was measured approximately every day. After administration of the experimental diets for 24 days, each of the groups were then continued on their respective diets and baseline evaluations were repeated as endpoint measures over the span of a week. At day 31, mice were anaesthetised with isoflurane, sacrificed by exsanguination and tissues were harvested.

Relative fat mass and lean body mass were quantified using a time-domain NMR whole-body composition analyzer (minispec LF90II, Bruker; MA, USA) and normalizing values to body weight. Maximal exercise capacity was measured by exercising mice on a treadmill at starting speed of 10 m/min and increasing the speed by 1 m/min every 1 min until exhaustion. Motor coordination, grip strength and balance were evaluated using a rotarod apparatus (Harvard Apparatus, MA).

Results

Figure 2:
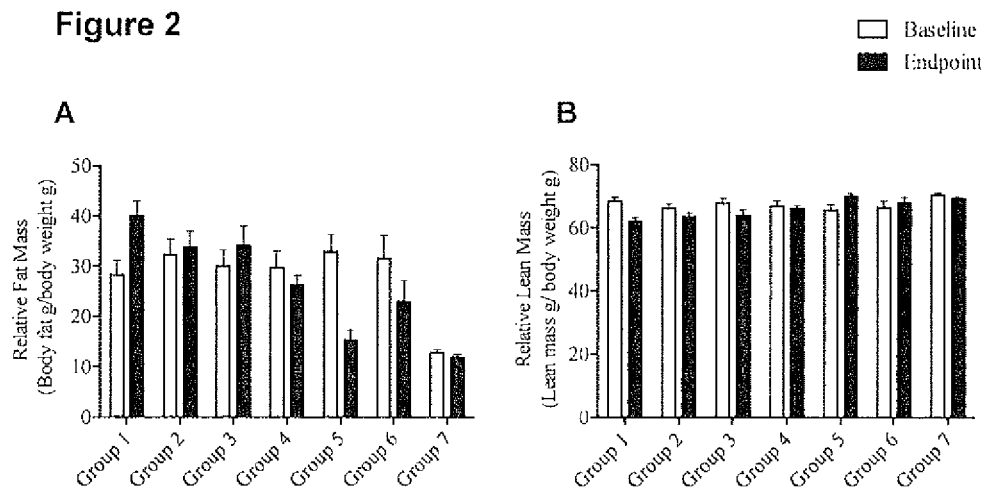
FIG. 2 graphically illustrates: A) relative fat mass, and B) relative lean mass of mice fed a weight management composition or a control diet and allocated to either sedentary or exercise training conditions for 30 days.
Figure 3:
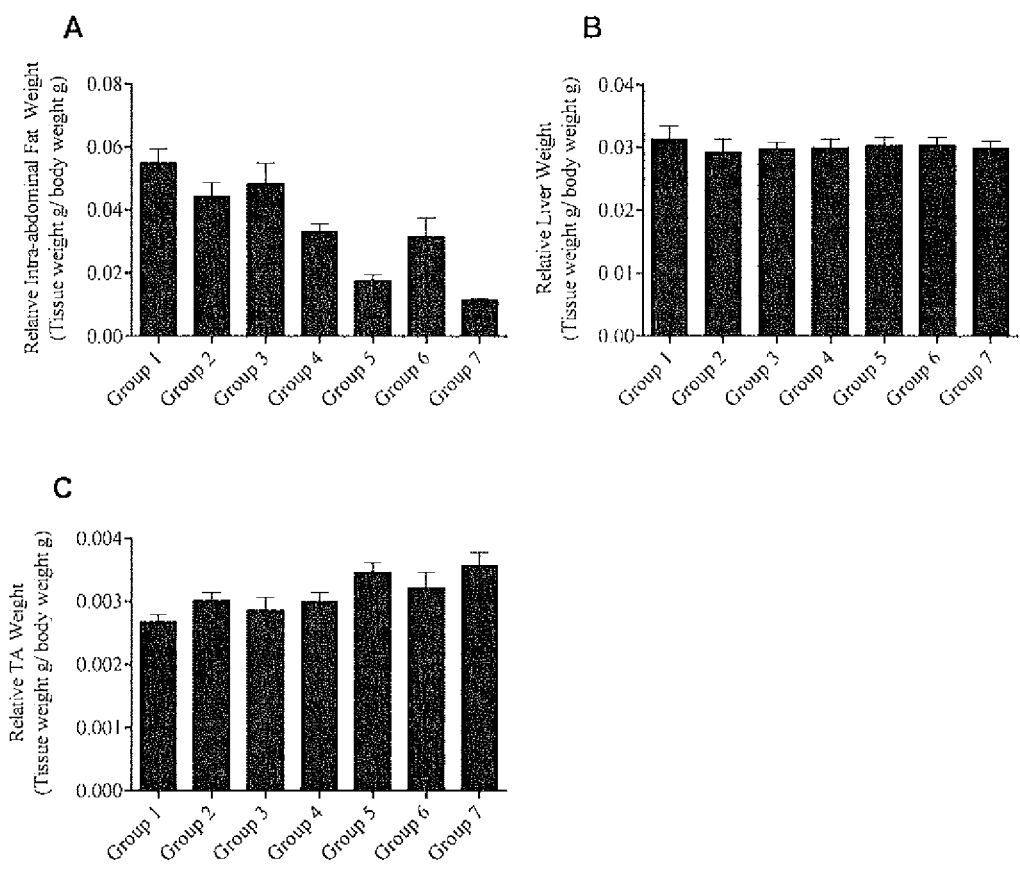
FIG. 3 graphically illustrates relative weight of the following tissues: A) intra-abdominal fat pad, B) liver and C) tibialis anterior muscle (TA; sum of both recorded) of mice fed a weight management composition or a control diet and allocated to either sedentary or exercise training conditions for 30 days.
Figure 4:
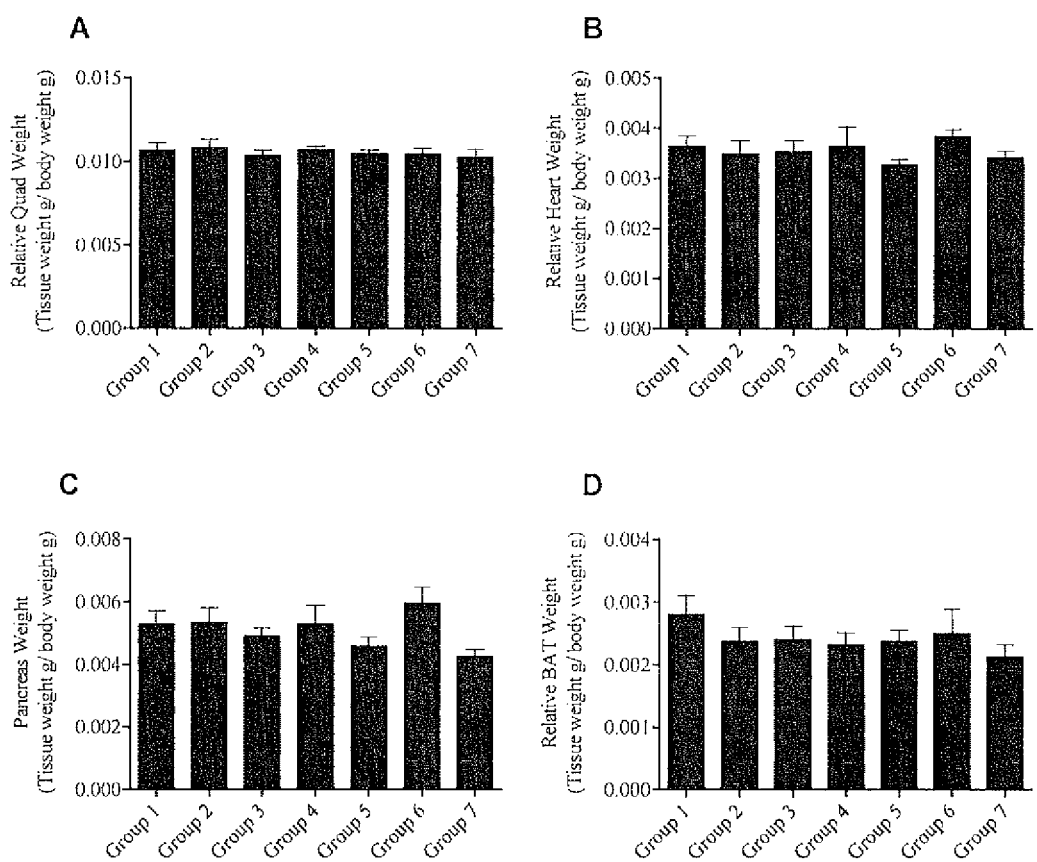
FIG. 4 graphically illustrates relative weight of the following tissues: A) quadriceps muscle (Quad; sum of both recorded), B) heart, C) pancreas and D) interscapular brown adipose tissue (BAT) of mice fed a weight management composition or a control diet and allocated to either sedentary or exercise training conditions for 30 days.

In order to determine the effects of the weight management composition comprising a weight loss agent and a mitochondria enhancing agent, body weight was recorded during 24 days of dietary supplementation (FIG. 1). As expected, mice fed the HFD control (Group 1) continued to gain weight throughout the entire study period and this HFD-induced weight gain was reduced in Groups 2 and 3. Surprisingly, after 24 days of supplementation, mice fed the Weight management combination A diet (Group 4) had a lower average body weight than that of the groups fed WL only diet (Group 2) or ME only diet (Group 3) alone, i.e. the weight management composition exhibited a synergistic or greater than additive effect with respect to weight loss. To evaluate how the Weight management combination A diet interacts with the effects of exercise, a second group fed this diet was subjected to an exercise regime for the 30 day period. Although mice in Group 6 were protected against any HFD-induced weight gain, weight loss in Group 5 was substantially greater, with Group 5 mice achieving a healthy body weight comparable to mice fed the Chow diet (Group 7) by only the $6^{th}$ day of supplementation and maintaining this desirable body weight throughout the remainder of the study. To gain an alternate perspective of the weight loss achieved, body composition was also measured by MRI. The relative fat mass of Group 1 was increased over time as anticipated at the endpoint measurement (FIG. 2A). While the mice in Groups 2 and 3 experienced little to no increase over the treatment period, the relative fat mass of Group 4 was reduced, despite the continued HFD feeding. Attesting to the synergistic weight loss achieved by administering the Weight management combination A diet in conjunction with exercise, mice in Group 5 experienced a 53% reduction in fat mass by endpoint in comparison with the 27% observed in Group 6. Small reductions in relative lean mass were experienced by Groups 1-3 (FIG. 2B). Importantly, this loss of lean mass was prevented in the Groups 4-7. Immediately following collection, tissue weights were recorded for an additional perspective of how the experimental diets affected body composition. Consistent with the previous findings, the relative weight of the intra-abdominal fat pads were lower in Groups 2 and 3 when compared to Group 1 and yet further reduced in Group 4 (FIG. 3A). Furthermore, the relative intra-abdominal fat pad weight of Group 5 was 68% lower than that of the sedentary HFD control Group 1, while Group 6 was only 43% lower than the same sedentary control. In contrast, there were no substantial differences between groups in the relative weights for liver (FIG. 3B), skeletal muscle (FIGS. 3C and 4A), heart (FIG. 4B), pancreas (FIG. 4C) or BAT (FIG. 4D).

Figure 5:
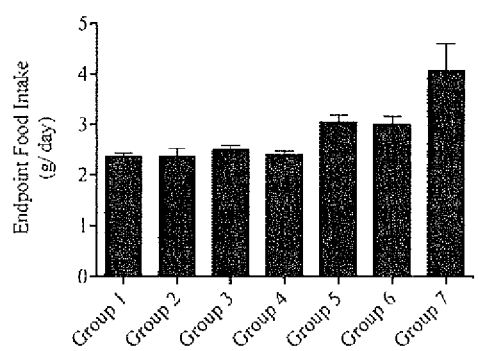
FIG. 5 graphically illustrates the food intake of mice at the endpoint timeline, when fed a weight management composition or a control diet and allocated to either sedentary or exercise training conditions for 30 days.

To evaluate if any of these changes in body weight and fat were resulting from appetite suppression or preferential consumption of any of the experimental compositions within the diets, food intake was monitored. As can be seen in FIG. 5, the food intake for sedentary mice in the Groups 1-4 were all similar. As would be expected due to the higher energy expenditure from exercise, mice in Groups 5 and 6 each ate approximately 25% more food than the sedentary mice. Similarly, although the mice fed Chow diet ate the most of any of the groups, this was also an expected outcome as the chow food is 40% less energy dense than the HFD.

Figure 6:
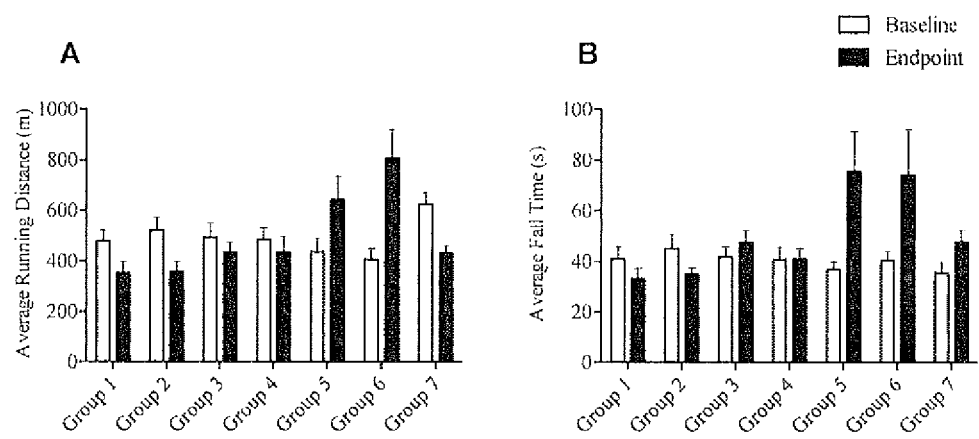
FIG. 6 graphically illustrates: A) maximal exercise capacity, and B) rotarod performance of mice fed a weight management composition or a control diet and allocated to either sedentary or exercise training conditions for 30 days.

To evaluate the effects of the diets on physical performance, a maximal exercise capacity test (FIG. 6A) was performed to determine how long the mice could run at a progressively increasing speed and a rotarod performance test (FIG. 6B) was conducted to quantify motor coordination, balance and grip strength. While mice in Group 1 and 2 experienced reductions in exercise capacity and rotarod performance over the supplementation period, mice in Groups 3 and 4 were protected against this HFD-induced impairment in performance. Consistent with the training effects from the exercise regime, mice in Groups 5 and 6 demonstrated markedly improved exercise capacity and rotarod performance by the time of the endpoint measure in comparison with baseline.

These data show that the weight maintenance composition is effective at improving weight maintenance in overweight or obese individuals.

Example 2—Alternate Versions of the Weight Management Composition Improve Body Weight, Body Fat and Mitochondrial Capacity In Vivo In order to confirm that alternate embodiments of the weight management composition could similarly reduce body weight and body fat and increase mitochondrial capacity as was observed in Example 1, a second study was conducted where HFD fed mice were administered diets containing 3 separate formulations of the weight management composition in conjunction with either exercise or no exercise (sedentary) for a period of 1 month.

All experiments were approved by the McMaster University Animals Ethics Committee and conducted under appropriate Canadian guidelines for animal research. 72 of C57/Bl6, diet-induced obesity mice were ordered from Jackson Laboratories, which were placed on a HFD (Teklad #TD.06414) containing 60% energy from fat at 6 weeks and fed ad libitum. At approximately 12 weeks of age, mice were allocated into experimental groups which where standardized by average body weight. Each of the experimental groups were fed one of the following HFDs containing 60% energy from fat: Group 8 were fed HFD control (referred to as HFD control diet; with energy density of 5.1 Kcal/g), Group 9 were fed the Weight management combination A diet from Example 1 (referred to as Weight management combination A diet; with energy density of 5.0 Kcal/g and containing weight loss agents in the following amounts: 0.25% green tea extract, 0.13% black tea extract, 0.25% green coffee bean extract, 0.25% conjugated linoleic acid and 0.005% forskolin by weight and mitochondria enhancing agents in the following amounts: 1% beetroot juice extract, 0.25% coenzyme Q10, 0.1% alpha lipoic acid and 1% creatine by weight and an additional 1000 IU/kg of vitamin E), Group 10 were fed an alternate weight management composition (referred to as Weight management combination B diet; with energy density of 5.0 Kcal/g and containing weight loss agents in the following amounts: 0.375% green tea extract, 0.25% green coffee bean extract, 0.25% conjugated linoleic acid and 0.005% forskolin by weight and mitochondria enhancing agents in the following amounts: 1% beetroot juice extract, 0.25% coenzyme Q10, 0.1% alpha lipoic acid and 1% creatine by weight and an additional 1000 IU/kg of vitamin E), Group 11 were fed a second alternate weight management composition (referred to as Weight management combination C diet; with energy density of 5.0 Kcal/g and containing weight loss agents in the following amounts: 0.375% green tea extract, 0.25% green coffee bean extract and 0.005% forskolin by weight and mitochondria enhancing agents in the following amounts: 1% beetroot juice extract, 0.25% coenzyme Q10 and 0.1% alpha lipoic acid by weight and an additional 1000 IU/kg of vitamin E). 12 mice per group for Groups 8-11 were then individually housed in standard microisolator cages and fed their respective diets for 1 month. To further evaluate the effects of the Weight management combination A diet on exercise, Group 13 consisted of another group of 12 mice which were fed the Weight management combination A diet, but were individually housed in cages containing an exercise wheel which allowed the mice to voluntarily exercise at will and were additionally exercised three times weekly on a treadmill at a speed of 15 m/min for 45 minutes. As a further control, Group 12 consisted of 12 mice which were fed the HFD control diet and subjected to the same housing and exercise regime as Group 13 in order to provide a reference to the effects of exercise alone on mice fed a HFD. Lastly, Group 14 consisted of 12 C57/Bl6 mice (Jackson laboratories, Cat. #000664), which were fed a standard mouse chow diet (referred to as Chow diet), with energy density of 3 Kcal/g; Envigo, diet #8640) from weeks 0-12, were housed in microisolator cages and continued on Chow diet for 30 days in order to serve as a third control, which demonstrates the effects of a healthy diet on body composition.

Beginning 7 days prior to the introduction of the experimental diets (i.e. day −7), baseline testing was conducted on all of the mice. Baseline testing included the following measurements: body weight, relative fat mass and lean body mass and maximal running capacity. On day 0, the experimental diets were introduced to all mice and the two exercise groups were placed in the running wheel cages and began the treadmill exercise regime. Body weight was measured daily throughout the study and food intake was measured weekly. After administration of the experimental diets for 1 month, each of the groups were then continued on their respective diets and baseline evaluations were repeated as endpoint measures over the span of a week. During the week following the 1 month treatment period, mice were anaesthetised with isoflurane, sacrificed by exsanguination and tissues were harvested. Relative fat mass, lean body mass and maximal exercise capacity was measured as described above.

Following tissue harvest, mitochondrial respiration was evaluated in permeabilized quadriceps muscle using high resolution respirometry (Oroboros Oxygraph-2k, Oroboros Instruments, Corp; Innsbruck, Australia). Complex 1 supported State 2 oxygen consumption was measured in the presence of 5 mM pyruvate, 2 mM malate and in the absence of ADP to provide an index of the uncoupling of mitochondrial substrate oxidation from the production of ATP. Complex I and II supported State 3 submaximal oxygen consumption was measured in the presence of 500 uM ADP, 2 mM Malate and 5 mM pyruvate was added to simulate complex I-supported respiration via NADH generation.

The proteins p62 and 4-HNE were evaluated in quadriceps muscle using the following antibodies in 5% milk in TBS: p62 (Cell Signalling, Cat. #51145) and hydroxynonenal (Abcam, Cat. #ab46545). RNA was isolated from the liver using RNeasy mini kits (Qiagen) and normalized to 2 µg before being reverse-transcribed to cDNA by using SuperScript Vilo cDNA synthesis kit (LifeTechnologies). The viia7 system (Thermofischer Scientific) in conjunction with FAST SYBR Green (Life Technologies) was used for quantitative real-time PCR assessment of mRNA species in liver. RNA was isolated from the intra-abdominal depot of white adipose tissue using the Trizol/chloroform method. The RNA (aqueous) phase was purified using the EZNA Total RNA Kit 1 (Omega Bio-Tek, Norcross, Ga., USA) as per the manufacturer's instructions. Samples were then reverse transcribed using a high capacity cDNA reverse transcription kit (SuperScript® VILO™ Master Mix; Invitrogen, cat. no. 11755050). Liver triglycerides were quantified using a commercially available kit (Abcam, ab65336) and protocol was carried out as per manufacturer's instructions. Lipid droplet staining was assessed in frozen liver sections using oil-red-O. Briefly, liver sections were washed in propylene glycol and exposed to an oil-red-O solution prepared in isopropanol. Sections were subsequently washed again in propylene glycol, counter stained with hematoxylin and mounted in an aqueous medium. Qualitative scoring of liver steatosis was performed by a trained pathologist using the following criterion: 0=none, none to rare affected cell, 1=mild, small clusters to up 50%, 2=moderate, 50% rare macroglobule and 3=extensive, diffuse numerous macroglobules. Serum alanine transaminase activity (ALT) was assessed using a commercially available kit (Cayman Chemical, 700260) and protocol was carried out as per manufacturer's instructions. Serum ApoB levels were quantified using a commercially available ELISA (Abcam, ab20737). Serum samples were diluted 1:5000 and protocol was carried out as per manufacturer's instructions. Serum ApoA1 levels were quantified using a commercially available ELISA (Abcam, ab238260). Serum samples were diluted 1:50,000 and protocol was carried out as per manufacturer's instructions. Serum PCSK9 levels were quantified using a commercially available ELISA (R and D Systems, MCP900). Serum samples were diluted 1:400 and protocol was carried out as per manufacturer's instructions.

To measure COX/CS ratio, quadriceps muscle was homogenized in Lysing Matrix D tubes (MP Biomedicals, Solon, Ohio, USA) using the FastPrep-24 Tissue and Cell Homogenizer (MP Biomedicals, Solon, Ohio, USA) for 5×5-second cycles at a speed of 4.0 m/s with samples placed on ice for 5 minutes between cycles. Samples were homogenized in 20 volumes of buffer containing 70 mM sucrose, 220 mM mannitol, 10 mM HEPES, 1 mM EGTA, supplemented with protease inhibitors (Complete Mini®, Roche Applied Science, Laval, PQ, Canada). For determination of citrate synthase maximal activity, 15 µl of muscle homogenate was added to cuvette containing: 825 µl 0.1M Tris Buffer (pH 8.0), 100 µl 5,5'-dithiobis(2-nitrobenzoic acid) (DTNB3, 0.5 mg/mL Tris Buffer) and 10 µl acetyl CoA (6 mg/mL Tris Buffer). The cuvette was warmed to 37° C., and 50 µL of oxaloacetate (6.1 mg/mL Tris buffer) was added to initiate the reaction. Absorbance was recorded at 412 nm for 120 seconds and the slope between 30 and 90 seconds was recorded. For COXIV activity, oxidized cytochrome c (Sigma C7752) was reduced by sodium dithionite in 0.05 M potassium phosphate buffer ($KH_2PO_4$, pH 7.4). Twenty microliters of muscle homogenate were added to 955 µL of 0.05 M potassium phosphate buffer and 30 µL of reduced cytochrome c in a cuvette that had been warmed to 37° C. The rate of oxidation of reduced cytochrome c was measured at 550 nm for 3 min at 37° C.

Results

Figure 7:
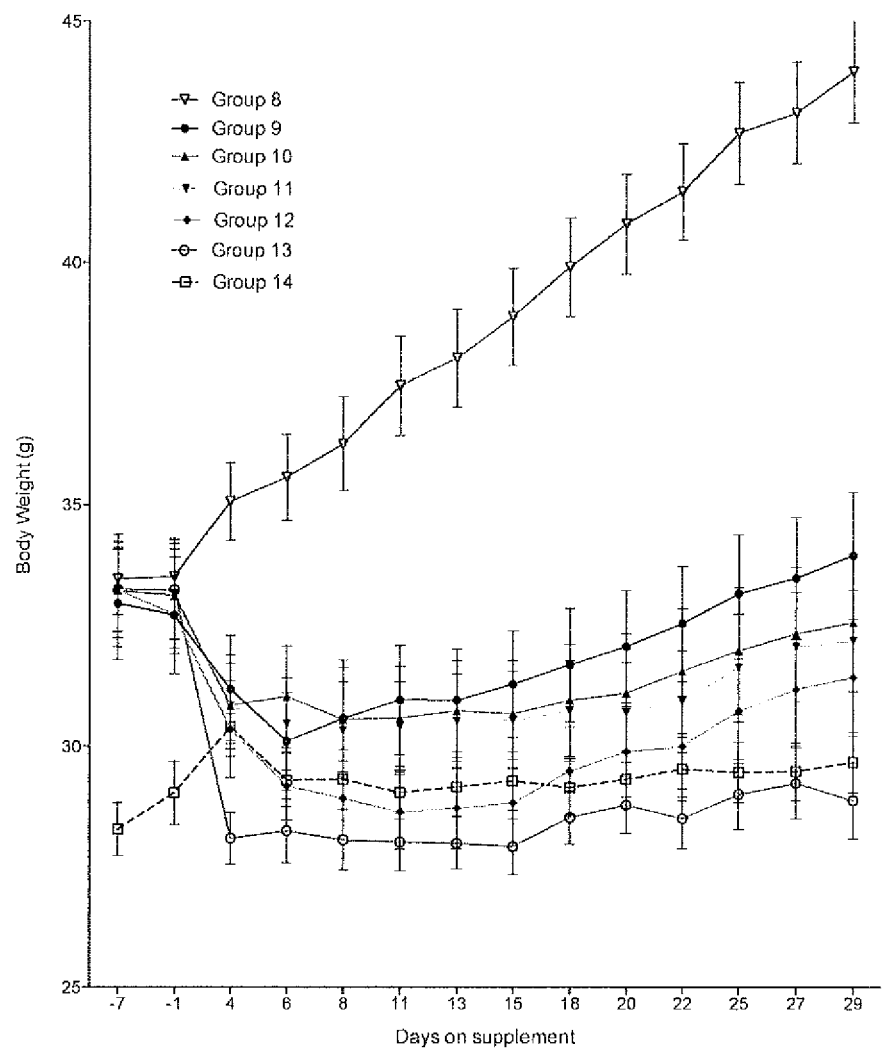
FIG. 7 graphically illustrates the body weight of mice fed various formulations of a weight management composition or a control diet and allocated to either sedentary or exercise training conditions for 30 days.
Figure 8:
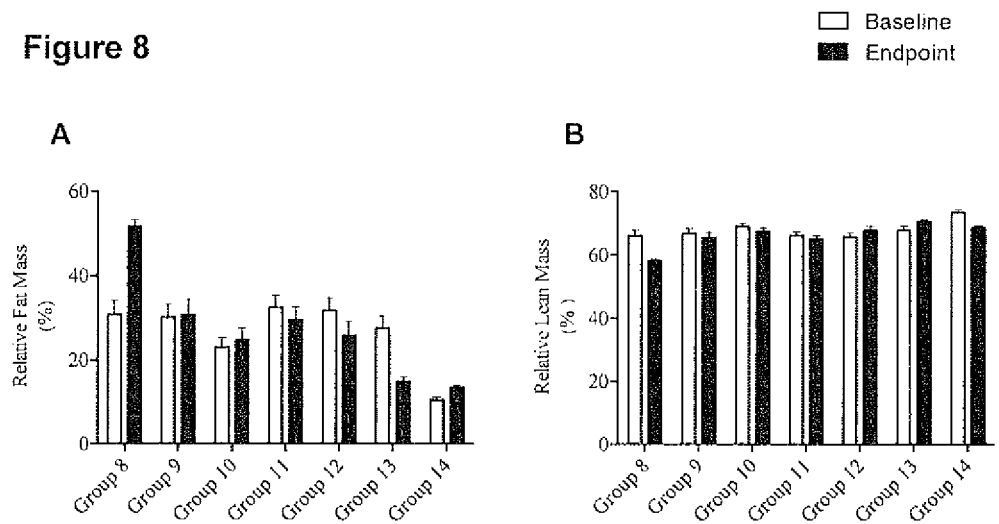
FIG. 8 graphically illustrates: A) relative fat mass, and B) relative lean mass of mice fed various formulations of a weight management composition or a control diet and allocated to either sedentary or exercise training conditions for 30 days.
Figure 9:
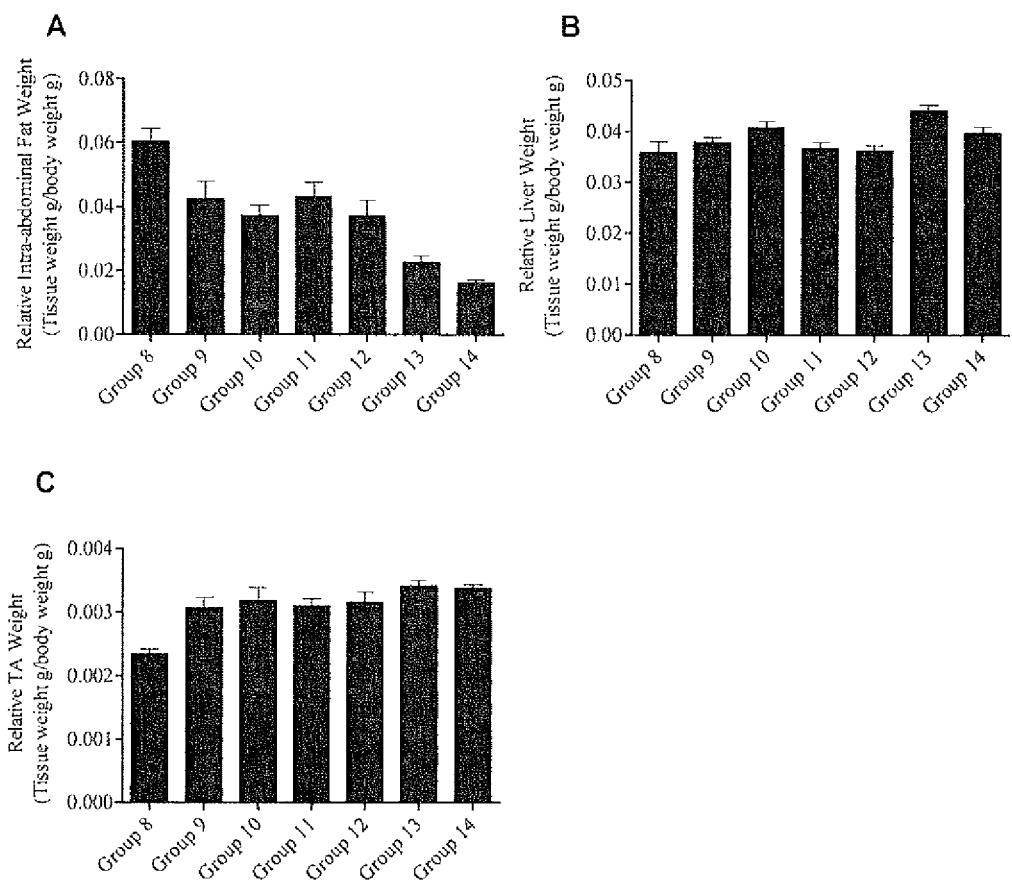
FIG. 9 graphically illustrates relative weight of the following tissues: A) intra-abdominal fat pad, B) liver and C) TA muscle (sum of both recorded) of mice fed various formulations of a weight management composition or a control diet and allocated to either sedentary or exercise training conditions for 30 days.
Figure 10:
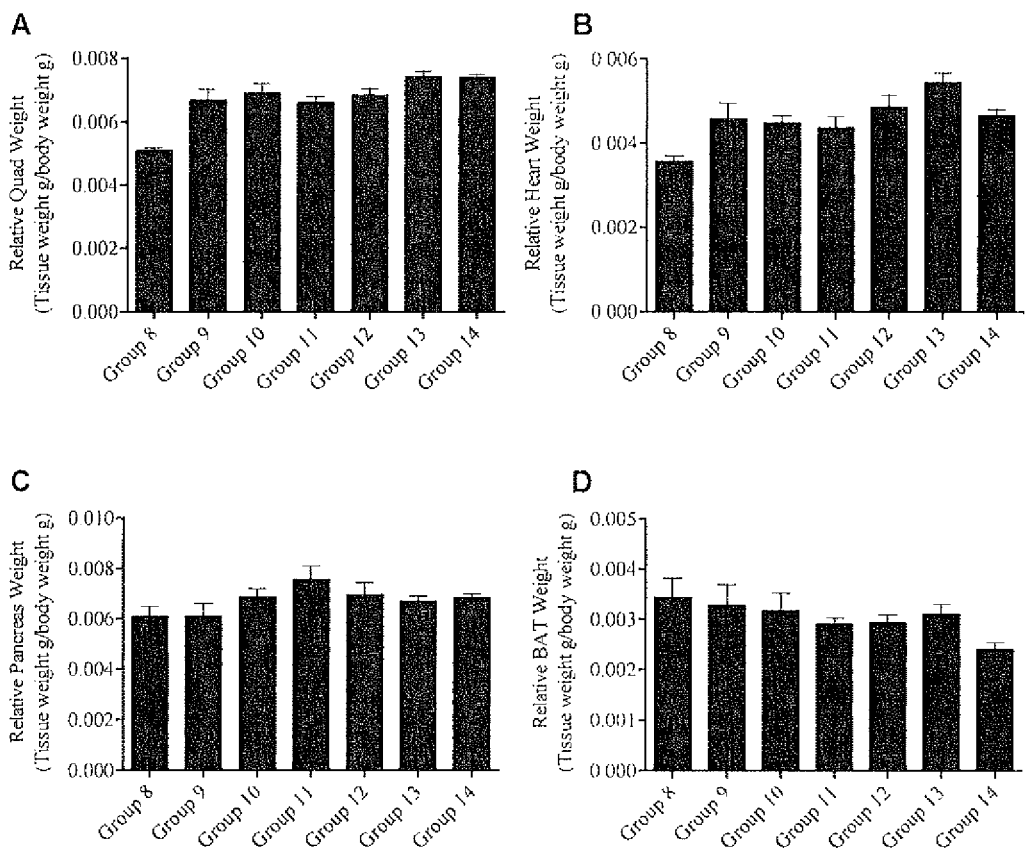
FIG. 10 graphically illustrates relative weight of the following tissues: A) Quad (sum of both recorded), B) heart, C) pancreas and D) interscapular BAT of mice fed various formulations of a weight management composition or a control diet and allocated to either sedentary or exercise training conditions for 30 days.
Figure 11:
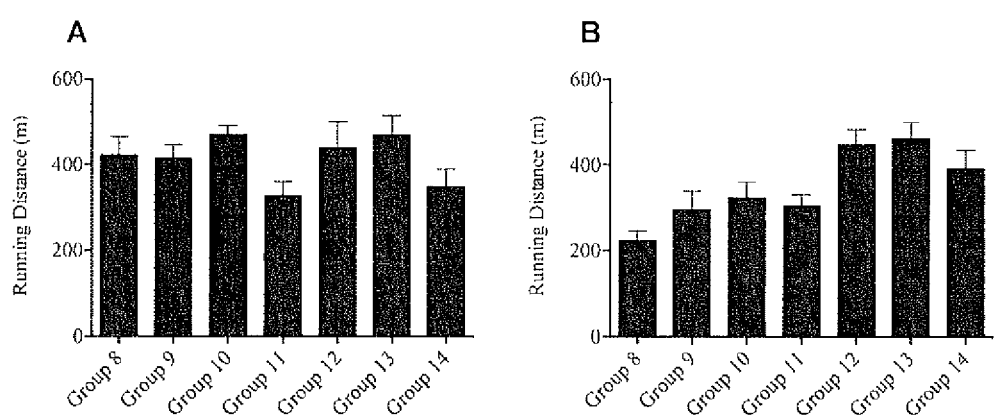
FIG. 11 graphically illustrates maximal exercise capacity at: A) baseline, and B) endpoint of mice fed various formulations of a weight management composition or a control diet and allocated to either sedentary or exercise training conditions for 30 days.

As expected, the body weight of mice fed the HFD control (Group 8) continually increased over the month long period, rising 31% higher than the day 0 weight (FIG. 7). Similar to the findings from Example 1, mice in group 9 fed the Weight management combination A diet had a substantially lower body weight after 1 month of supplementation when compared to Group 8. Importantly, mice in Group 10, 11 and 12 experienced a similar protection from HFD-induced weight gain, losing 2, 3 and 4% of the starting body weight amounts respectively, despite the month of HFD feeding. As seen in Example 1, mice fed the Weight management combination A diet in addition to being administered exercise (Group 13) had the greatest amount of weight loss of all groups (a reduction of 13%) and maintained a body weight similar to that of mice fed the Chow diet (Group 14). For a second measure of body mass, fat (FIG. 8A) and lean mass (FIG. 8B) were measured via MRI. As would be predicted by the body weight findings, the relative fat mass of Group 8 increased by 68% from the starting amount, while there were little to no increase in fat mass observed in Groups 9-11. The relative fat mass of mice in Group 12 was reduced by 19% and mice in Group 13 lost 46% of fat in comparison to the starting amount. No large differences were observed between the lean mass of any HFD groups, with the exception that relative lean mass was 12% reduced in Group 8 from the starting amount. For a third measure of body composition, tissue weights were determined. The relative intra-abdominal fat depot weights for each of the 3 groups administered one of the Weight management combination diets (Groups 9-11) and Group 12 were between 29-39% lower than the HFD control Group 8, while the exercise and Weight management combination A diet Group 13 had 63% less intra-abdominal fat than Group 8 (FIG. 9A). Liver (FIG. 9B), skeletal muscle (FIGS. 9C and 10A), heart (FIG. 10B), pancreas (FIG. 10C) and BAT (FIG. 10D) weights were comparable between groups, with the exception that the relative liver, skeletal muscle and heart weights were lower in Group 8. To evaluate the effects of the weight management composition on aerobic capacity, an exercise capacity test was performed at baseline (FIG. 11A) and endpoint (FIG. 11B). After the one month experimental period, maximal running distance for Group 8 was 47% lower. Suggesting some further protection against the negative effects of the HFD, Groups 9-11 experienced lessor reductions of 29%, 31% and 7% respectively. Both of Groups 12 and 13 were completely protected against HFD-induced reductions of exercise capacity. These findings demonstrate that the weight management composition is effective for improving weight management.

Figure 12:
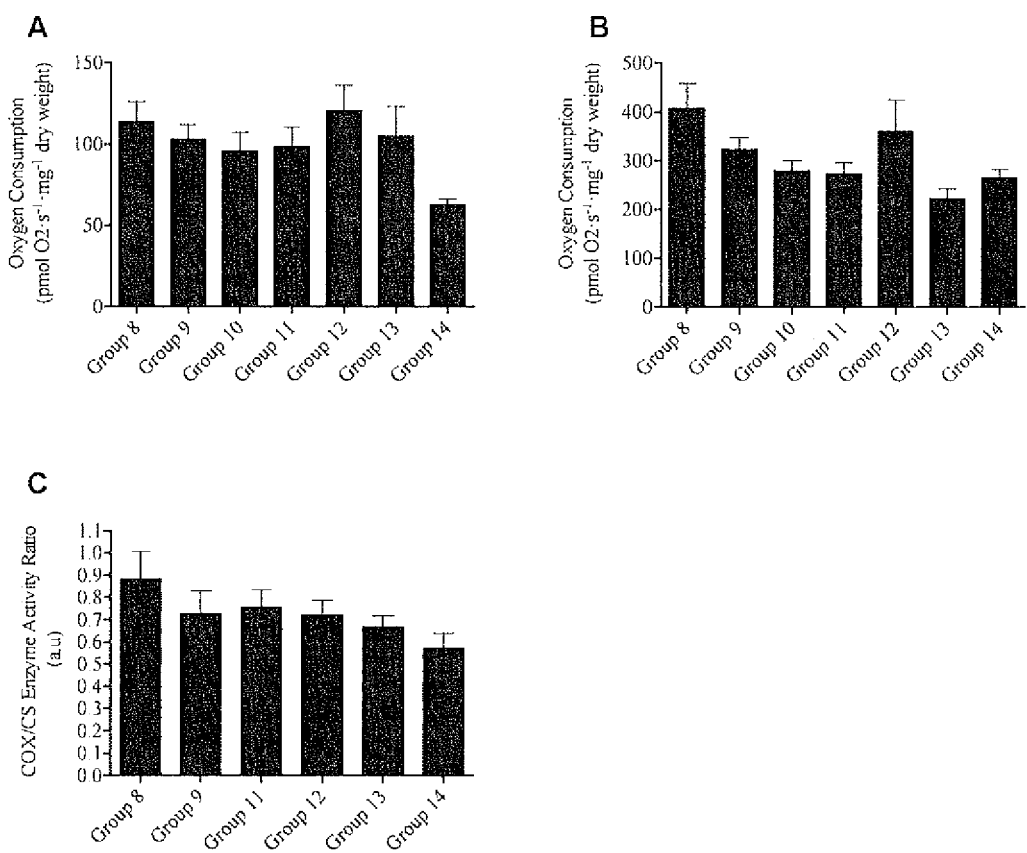
FIG. 12 graphically illustrates skeletal muscle: A) Complex 1, State 2 uncoupled mitochondrial respiration, B) Complex I and II supported State 3 submaximal oxygen consumption, and C) ratio of COXIV enzyme activity to citrate synthase (COX/CS) enzyme activity of mice fed various formulations of a weight management composition or a control diet and allocated to either sedentary or exercise training conditions for 30 days.

High resolution oxygen consumption measurements were obtained from quadriceps muscle in order to evaluate the skeletal muscle mitochondrial capacity of mice administered the weight management composition. Complex 1 supported State 2 respiration in the absence of ADP was first measured to provide an indicator for uncoupled respiration (FIG. 12A). Mice in the Chow diet fed Group 14 demonstrated a 45% lower amount of uncoupled oxygen consumption when compared to the HFD control Group 8. Surprisingly, each of the groups administered one of the Weight management combination diets (Groups 9-11 and 13) experienced a decrease of uncoupled oxygen consumption when compared to Group 8. Complex 1 and II supported State 3 submaximal oxygen consumption was next measured to determine the skeletal muscle mitochondrial capacity to perform cellular respiration in the presence of fuel substrates. Similar to uncoupled respiration, ADP-stimulated oxygen consumption in Chow diet fed Group 14 was lower than that of the HFD control Group 8 and each of the groups administered one of the Weight management combination diets (Groups 9-11 and 13) had a respiration rate that was comparable to Chow diet fed Group 14 (FIG. 12B). For an alternate measure of mitochondrial capacity in skeletal muscle, the ratio of enzyme activity of cytochrome c oxidase IV, the final enzyme in the electron transport chain) and citrate synthase (a biomarker of mitochondrial density) was determined (FIG. 12C). In comparison to the HFD control Group 8, all groups had a lower cytochrome c oxidase IV to citrate synthase activity ratio, with Group 14 having the lowest ratio. Collectively, these measures of skeletal muscle mitochondrial function suggest that the HFD is inducing a compensatory upregulation of mitochondrial activity in skeletal muscle and that the weight management composition protects HFD fed mice against these changes to maintain the mitochondria functioning in a state more similar to healthy Chow diet fed mice.

Figure 13:
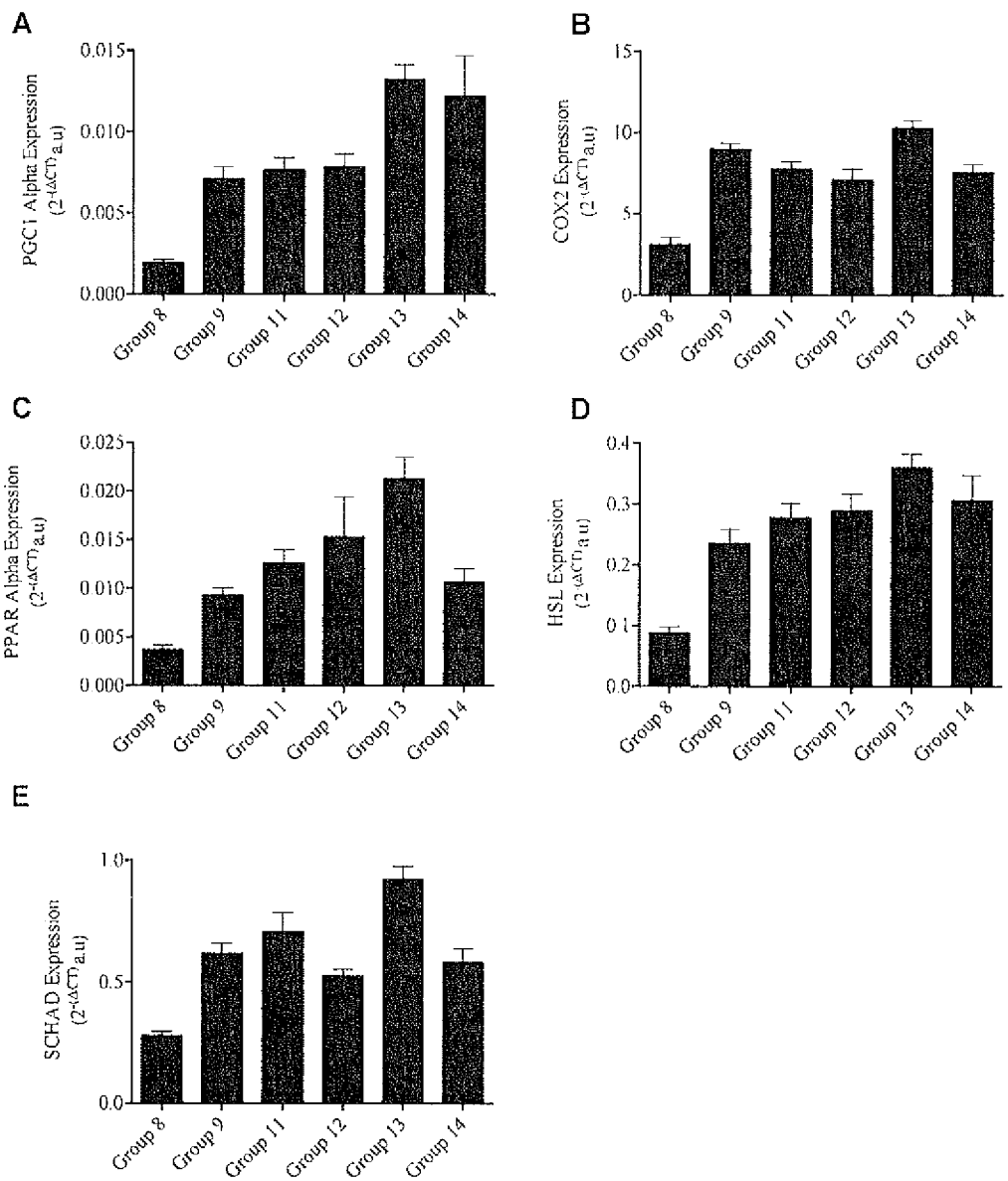
FIG. 13 graphically illustrates the white adipose tissue mRNA expression of fat oxidation and mitochondrial capacity biomarkers: A) PGC1 alpha, B) COX2, C) PPAR alpha, D) HSL and E) SCHAD of mice fed various formulations of a weight management composition or a control diet and allocated to either sedentary or exercise training conditions for 30 days.

To evaluate the effects of the weight management composition on adipose tissue mitochondrial capacity, the mRNA expression of genes critical to mitochondrial function and lipid oxidation were measured in white adipose tissue. PGC1 alpha is a transcriptional coactivator that is considered to be one of the primary promotors of mitochondrial biogenesis. PGC1 alpha expression was increased by approximately 4-fold in Groups 9, 11 and 12 in comparison to Group 8. Interestingly, PGC1 alpha expression was increased 6.0-fold and 6.4-fold in Group 13 and 14, respectively (FIG. 13A). COX2 is one of the subunits of citrate synthase, a biomarker of mitochondrial density, and was lowest in the HFD control Group 8 (FIG. 13B). In mice administered one of the Weight management combination diets or exercised, COX2 expression was increased to a level equal to or greater than that seen in Chow fed mice. PPAR alpha, HSL and SCHAD are three key genes that collectively, promote the breakdown of stored triglycerides into fatty acid chains, the tissue uptake of fatty acids and fatty acid oxidation in the mitochondria. The expression of PPAR alpha (FIG. 13C), HSL (FIG. 13D) and SCHAD (FIG. 13E) were markedly lower in the HFD control Group 8 compared with the Chow diet fed Group 14. Similar to the pattern observed for the mitochondrial biogenesis genes above, the mRNA expression levels for these genes were all elevated in mice administered one of the Weight management combination diets or exercised to a level that was equal to or greater than that seen in Chow fed mice. These findings indicate that the mitochondrial capacity of white adipose tissue is improved in mice administered the weight management composition, thus promoting the use of stored fat for energy expenditure and weight maintenance.

Figure 14:
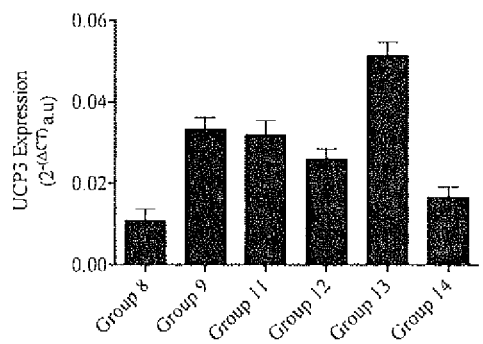
FIG. 14 graphically illustrates the white adipose tissue mRNA expression of white adipose tissue browning biomarkers: A) uncoupling protein 3 (UCP3), B) PRDM16, C) CIDEA and D) ADIPOQ of mice fed various formulations of a weight management composition or a control diet and allocated to either sedentary or exercise training conditions for 30 days.
Figure 14:
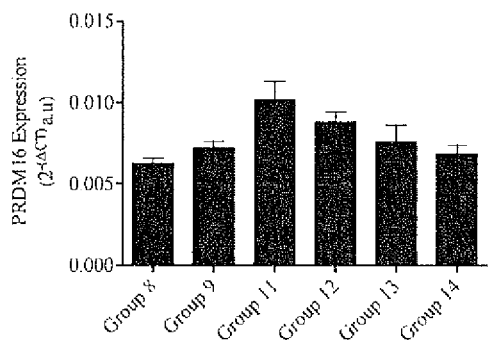
Figure 14:
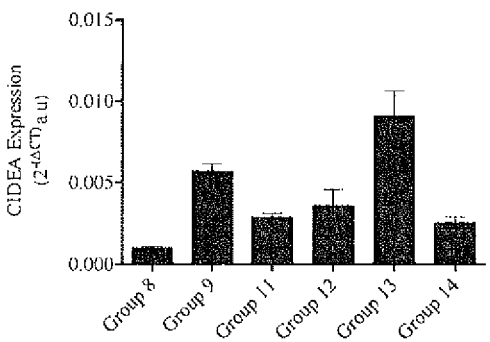
Figure 14:
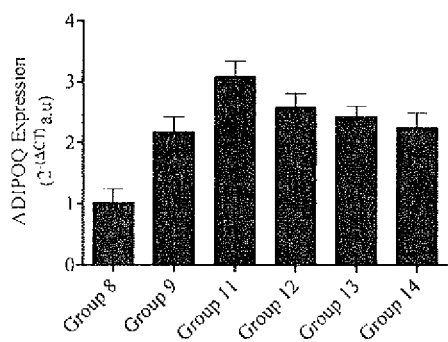

An increased abundance and activity of mitochondria in white adipose tissue is indicative of a transdifferentiation or browning into the more metabolically active beige adipose tissue. In addition to the above described increased gene expression of PGC1 alpha and PPAR alpha, which are classical genes of the browning pathway, the expression of other beige adipose tissue biomarkers were evaluated. In comparison to the HFD control Group 8, the expression of uncoupling protein 3 (UCP3) was 53% higher in the Chow diet fed Group 14 and between 2.9 to 4.7-fold higher in mice fed one of the Weight management combination diets (Groups 9, 11 and 13) (FIG. 14A). Similar to UCP3, the gene expression of the browning biomarkers PRDM16 (FIG. 14B), CIDEA (FIG. 14C) and ADIPOQ (FIG. 14D) were all elevated in mice administered one of the Weight management combination diets, exercised or fed chow diet in comparison to the lower levels of HFD fed control Group 8. These findings suggest that further to the enhanced fat oxidation and mitochondrial capacity observed, that the weight management composition is also inducing a browning of white adipose tissue. This enhanced browning is desirable for weight management as it would be expected to increase thermogenesis and thus, promote energy expenditure from the fat stores.

Figure 15:
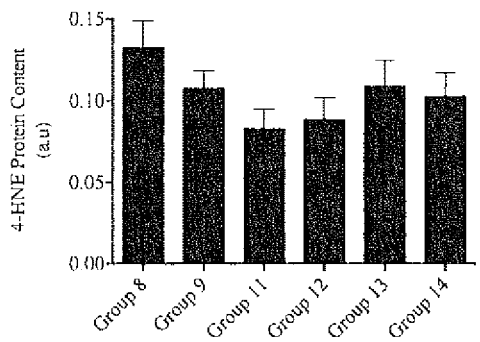
FIG. 15 graphically illustrates the skeletal muscle abundance of: A) 4-HNE and B) p62 of mice fed various formulations of a weight management composition or a control diet and allocated to either sedentary or exercise training conditions for 30 days.
Figure 15:
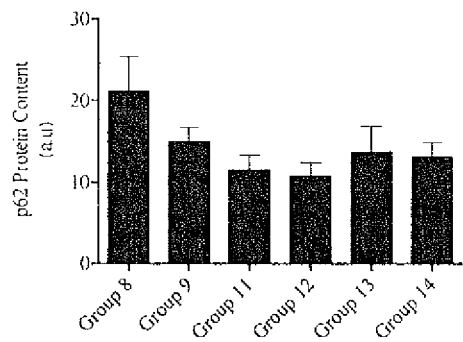

To determine if the weight management composition exerts an effect on oxidative stress, the amount of trans-4-hydroxy-2-nonenal (4-HNE) in skeletal muscle was measured. 4-HNE is generated as a product of the lipid peroxidation reaction and is a validated biomarker of oxidative stress. 4-HNE was 29% higher in the HFD fed control Group 8 compared with the Chow diet fed Group 14 (FIG. 15A). Unexpectedly, relative to Group 8, the amount of 4-HNE was also between 18 and 37% lower in mice administered one of the Weight management combination diets or exercised (Groups 9 and 11-13). Oxidative stress is known to oxidatively damage cellular components and promote the degradation of those cellular materials by the autophagy pathway. The accumulation of p62 is an indicator of oxidative stress and the amount of cellular components which are targeted for degradation by the autophagy pathway. In accordance with the 4-HNE results, p62 abundance was between 30 and 49% lower in mice administered one of the Weight management combination diets, exercised or fed chow diet (FIG. 15B). These results show that the weight management composition is effective for improving oxidative stress.

Figure 16:
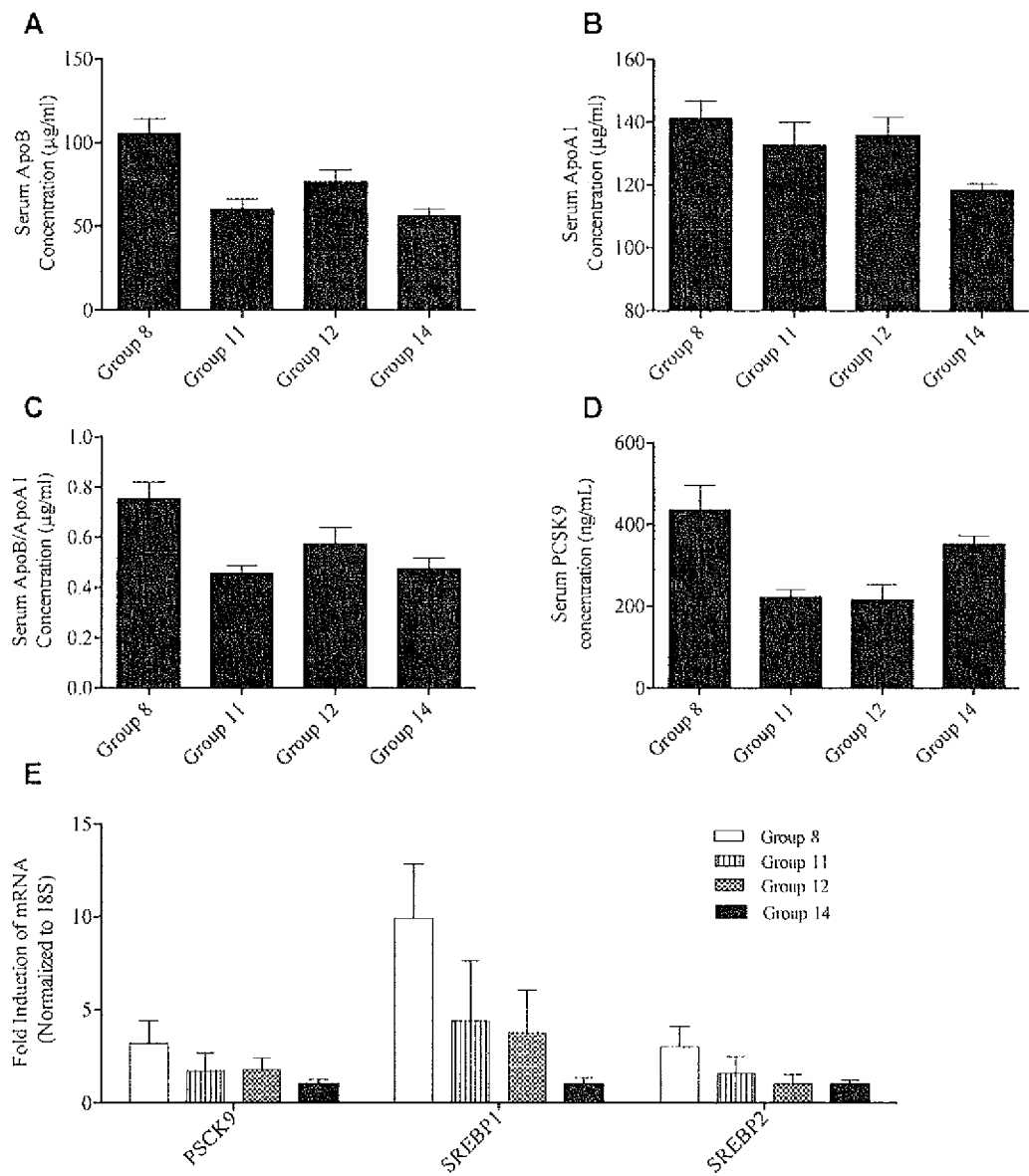
FIG. 16 graphically illustrates: A) serum ApoB concentration, B) serum ApoA1 concentration, C) serum ApoB/ApoA1, D) serum PCSK9 concentration, and E) liver lipid synthesis and cholesterol uptake biomarker gene expression of mice fed various formulations of a weight management composition or a control diet and allocated to either sedentary or exercise training conditions for 30 days.

To determine the effects of the weight management composition on dyslipidemia, serum levels of ApoB and ApoA11 were measured (FIG. 16A-C). As would be predicted, the ratio of ApoB/ApoA1 was 59% higher in the HFD fed Group 8 compared with the Chow diet fed Group 14. Unexpectedly, the HFD-induced elevation of ApoB/ApoA1 levels was prevented in Group 11 and 12. PCSK9 is an enzyme which raises LDL cholesterol levels by degrading the LDL receptor protein that is required for transporting LDL into tissues. The concentration of serum PCSK9 in Group 8 was 24% higher than in Chow diet fed Group 14 (FIG. 16D). Conversely, serum PCSK9 in mice fed the Weight management combination diet and exercised (Group 11 and 12) were both approximately 50% lower than Group 14. This finding of a protection against HFD induced increase of PCSK9 in Groups 11 and 12 was also observed in liver mRNA expression levels (FIG. 16E). Supporting this observation, both the weight management combination and exercise similarly protected the mice from a HFD-induced rise in liver mRNA expression of SREBP1 and SREBP2, two of the main promotors of cholesterol, fatty acid, triglyceride and phospholipid synthesis (FIG. 16E). These findings demonstrate that the weight management composition is effective at treating dyslipidemia by improving blood lipid levels.

Figure 17:
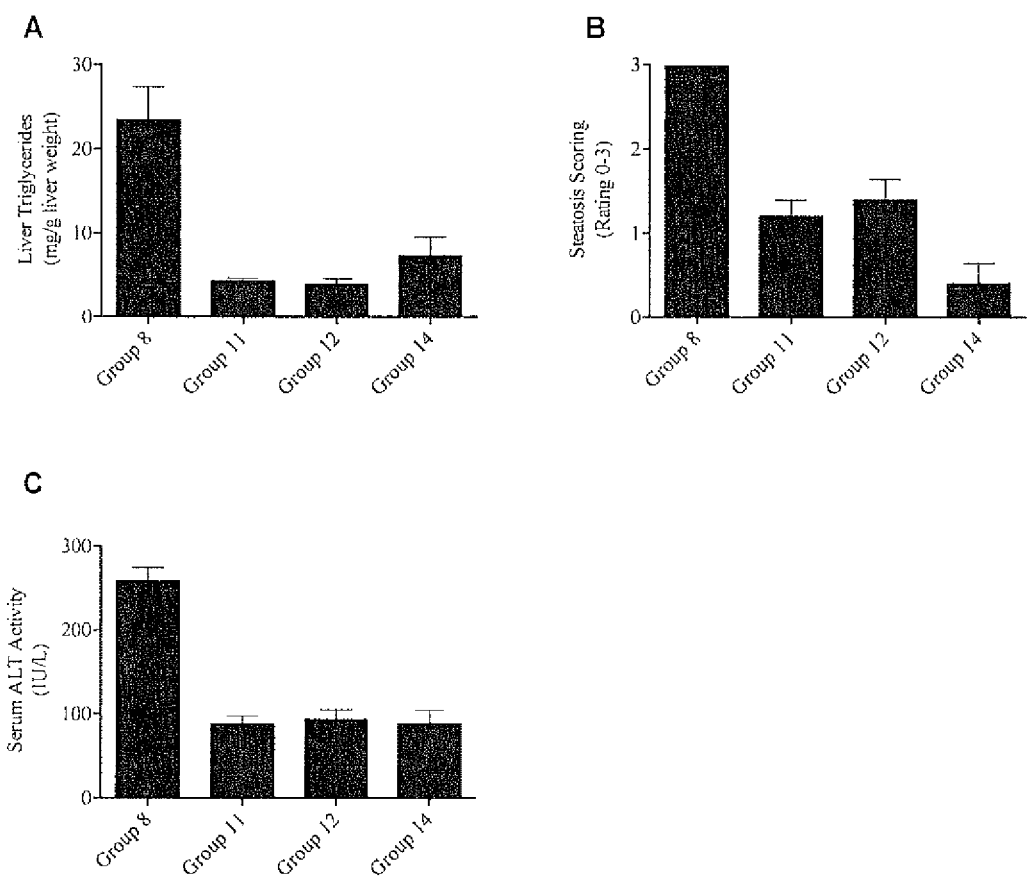
FIG. 17 graphically illustrates: A) liver triglycerides, B) liver steatosis scoring, and C) serum ALT activity of mice fed various formulations of a weight management composition or a control diet and allocated to either sedentary or exercise training conditions for 30 days.
Figure 18:
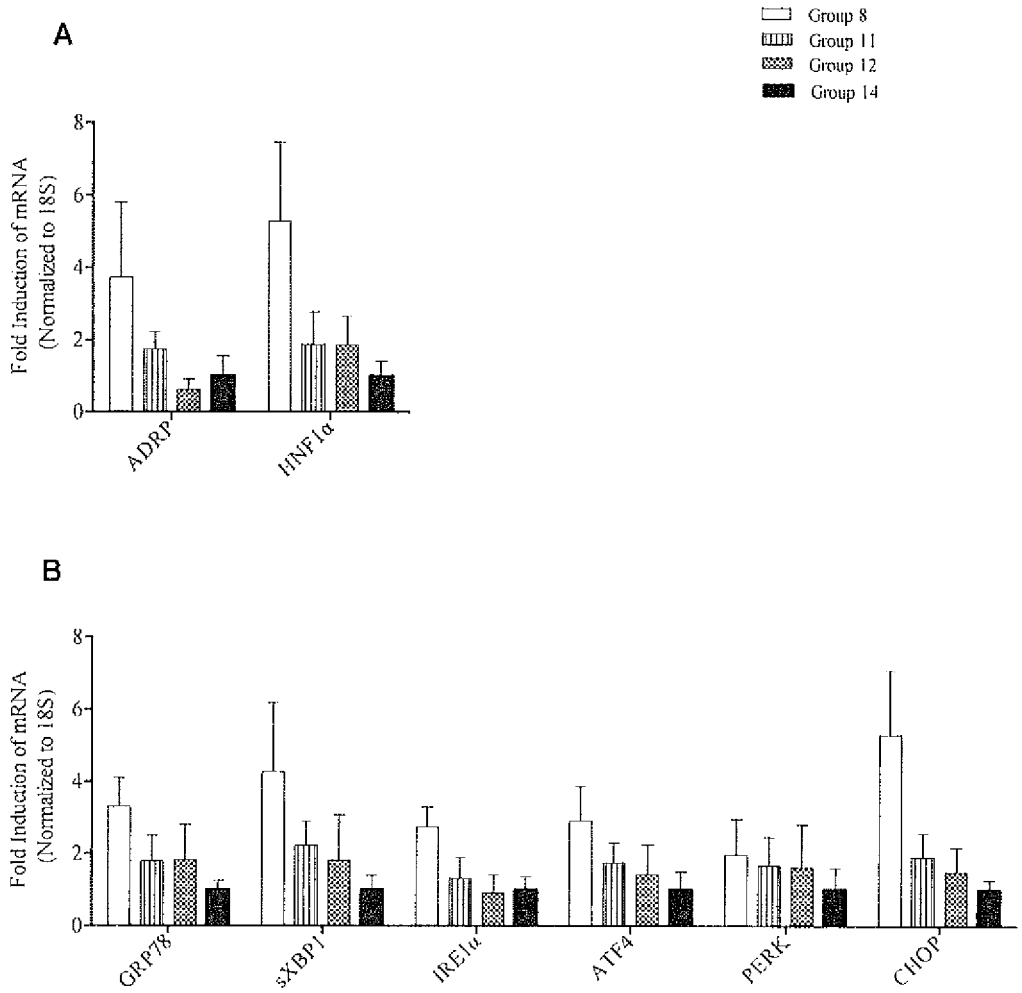
FIG. 18 graphically illustrates: A) liver lipid synthesis biomarker gene expression, and B) liver endoplasmic reticulum stress biomarker gene expression of mice fed various formulations of a weight management composition or a control diet and allocated to either sedentary or exercise training conditions for 30 days.
Figure 19:
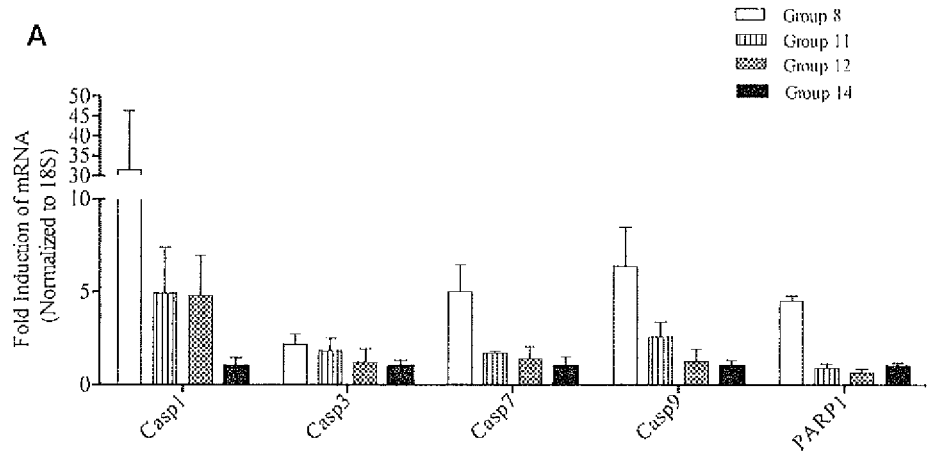
FIG. 19 graphically illustrates: A) liver programmed cell death biomarker gene expression, and B) liver inflammation and fibrosis biomarker gene expression of mice fed various formulations of a weight management composition or a control diet and allocated to either sedentary or exercise training conditions for 30 days.
Figure 19:
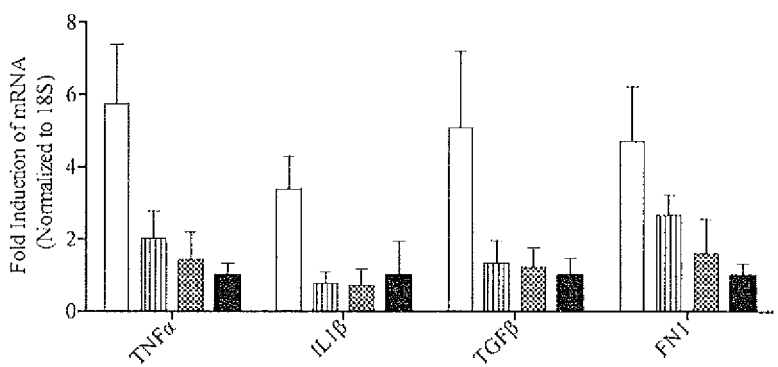

To evaluate if the weight management composition has an effect on liver health, several markers of fatty liver disease were measured. The amount of triglycerides in the liver of HFD fed Group 8 was 3.2-fold higher than those quantified in Chow fed Group 14 (FIG. 17A). Conversely, both the exercised Group 12 and the Weight management combination C diet Group 11 demonstrated liver triglyceride levels even lower than Group 14. This observation that the weight management composition reduced liver triglycerides and conferred protection against the development of fatty liver was also visually confirmed by a trained pathologist who provided a steatosis score for oil-red-O liver sections from each of the groups (FIG. 17B). Blood alanine aminotransferase (ALT) levels are used clinically as an indicator of hepatocellular injury or liver cell death. Serum ALT levels were elevated 2.9-fold in HFD fed Group 8 compared with Chow diet fed Group 14, but remained unchanged in Groups 11 and 12 (FIG. 17C). To investigate a potential cause for excess lipid accumulation in the livers of HFD fed mice, and the presence of normal lipid levels in HFD mice supplemented with the weight management composition, mRNA expression levels of key liver proteins were evaluated. SREBP1, SREBP2, ADRP, and HNF1 alpha are 4 of the key genes that regulate liver lipid levels. The mRNA expression for these 4 genes were all substantially increased in Group 8 compared to Group 14 and for each protein, Group 11 demonstrated a reduction of mRNA expression level that was consistent with Group 12 which engaged in daily exercise (FIGS. 16E and 18A). The unfolded protein response (UPR) occurs in response to increased endoplasmic reticulum stress, which may be caused by and further promote hepatocellular injury. GRP78, sXBP1, IRE1 alpha, ATF4, PERK and CHOP are 6 of the primary genes which effect the UPR and during prolonged endoplasmic reticulum stress, direct the cell towards apoptosis. mRNA expression for each of these UPR proteins were between 2 and 5.3-fold higher in the livers of HFD fed Group 8 mice compared to Chow diet fed Group 14 (FIG. 18B). Daily exercise reduced this HFD-induced increase in UPR markers of Group 12, a protective effect that was mirrored in Group 11 fed the Weight management combination C diet. Casp1, Casp3, Casp7, Casp9 and PARP1 are 5 of the key genes which are promotors of apoptosis, pyroptosis, necroptosis and inflammation that initiate and effect programmed cell death. Similar to the pattern observed in lipid accumulation and endoplasmic reticulum stress genes, the mRNA expression of these programmed cell death proteins were markedly elevated in the livers of Group 8 and lowered toward normal values in Groups 11 and 12 (FIG. 19A). Inflammation and hepatocyte death are two hallmarks of the second stage of fatty liver disease known as steatohepatitis. Both the liver mRNA expression levels of TNF alpha and IL-1 beta, two key regulators of the inflammation cascade, were between 3.4 and 5.8-fold higher in Group 8 compared with Group 14 (FIG. 19B). To the contrary, the levels of these inflammatory markers were at or near the healthy levels of Chow diet fed mice in Groups 11 and 12. Chronic inflammation is associated with the development of liver fibrosis, a hallmark of the third stage of fatty liver disease. TGF beta and FN1 are two of the primary genes associated with the development of liver fibrosis. As with the inflammation genes, the liver expression of fibrosis markers were greatly elevated in Group 8 and lowered at or near the level of Chow diet fed mice in Groups 11 and 12 (FIG. 19B). These results demonstrate that the weight management composition is effective for improving fatty liver disease.

Figure 20:
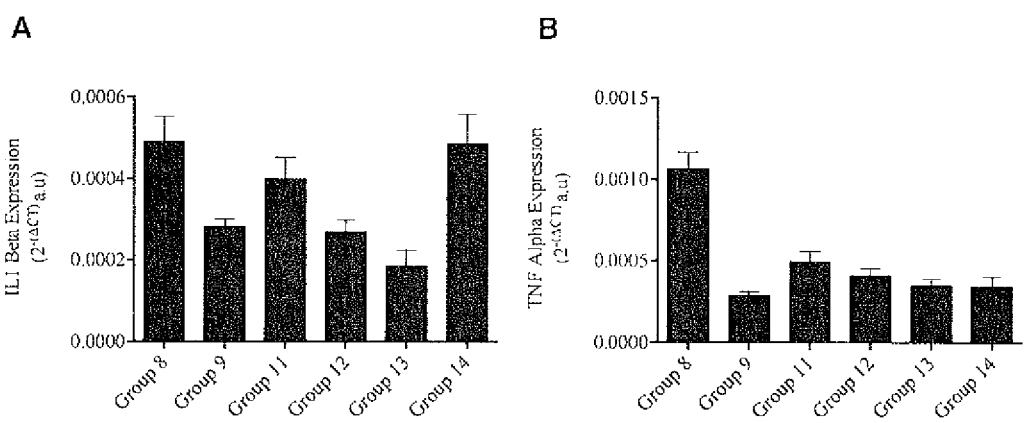
FIG. 20 graphically illustrates the white adipose tissue mRNA expression of the systemic inflammation biomarkers: A) IL1 beta and B) TNF alpha of mice fed various formulations of a weight management composition or a control diet and allocated to either sedentary or exercise training conditions for 30 days.

In order to determine if the weight management composition can improve systemic inflammation levels, inflammatory biomarkers were evaluated in tissues. As shown above, TNF alpha and IL-1 beta expression was considerably lower in the livers of Groups 11, 12 and 14 when compared to the Group 8 (FIG. 20A). Accordingly, mRNA expression of IL1 beta in white adipose tissue was lower in each of the groups administered the Weight management combination diets or exercised (Groups 9 and 11-13) in comparison to the HFD control Group 8. The mRNA expression of TNF alpha in white adipose tissue was between 2.2 and 3.7-fold elevated when compared to Groups 9 and 11-13 (FIG. 20B). These observations of reduced inflammation in white adipose tissue and the liver demonstrate that the weight management composition is able to effectively reduce systemic inflammation levels.

These findings clearly show that administration of the weight management composition treated or improved weight management, mitochondrial capacity, fatty liver disease, dyslipidemia, oxidative stress levels, brown adipose tissue activity and systemic inflammation levels.

Example 3—Alternate Versions of the Weight Management Composition Improve Fat Oxidation In Vivo In order to evaluate some of the possible means by which the weight management composition reduces body weight or body fat to promote weight management, HFD fed mice were placed in metabolic cages while being administered the weight management composition.

All experiments were approved by the McMaster University Animals Ethics Committee and conducted under appropriate Canadian guidelines for animal research. 24 of C57/Bl6, diet-induced obesity mice were ordered from Jackson Laboratories, which were placed on a HFD (Teklad #TD.06414) containing 60% energy from fat at 6 weeks and fed ad libitum. At approximately 12 weeks of age, mice were allocated into experimental groups which where standardized by average body weight, placed in the metabolic cages (Columbus Lab Animal Monitoring System; Columbus instruments) and allowed to acclimate to the new environment for about 12 hours. Following the acclimation period, mice remained on the 60% HFD used in Groups 1 and 8 above for a period of 1 day to collect metabolic data for each group while being fed the control HFD and prior to any treatment. After 24 hours of measurements (i.e. at the end of day −1) on the control HFD, mice were administered diets based on their allocation to the following groups: Group 15 were administered the same 60% HFD control as they were previously on, Group 16 were administered the Weight management combination A diet from Example 1 and 2 and Group 17 were administered the Weight management combination C diet from Example 2. As a standard low-fat diet control, a group of 8 mice (Group 18) which had been raised on Chow diet from Example 1 and 2 remained on Chow diet throughout the study. Following Day −1, measurements were collected for 3 days (referred to as Days 1-3) to observe any changes in metabolic activity during administration of the experimental diets. Lipid oxidation rates were collected by indirect calorimetry and were calculated based on the following equation $(1.6946*VO2)-(1.7012*VCO2)$. Activity levels were collected by measured beam breaks across the x-axis of the metabolic cages.

Results

During Day −1, fat oxidation rates were comparable between each of the three groups on the control HFD (FIG.

Figure 21:
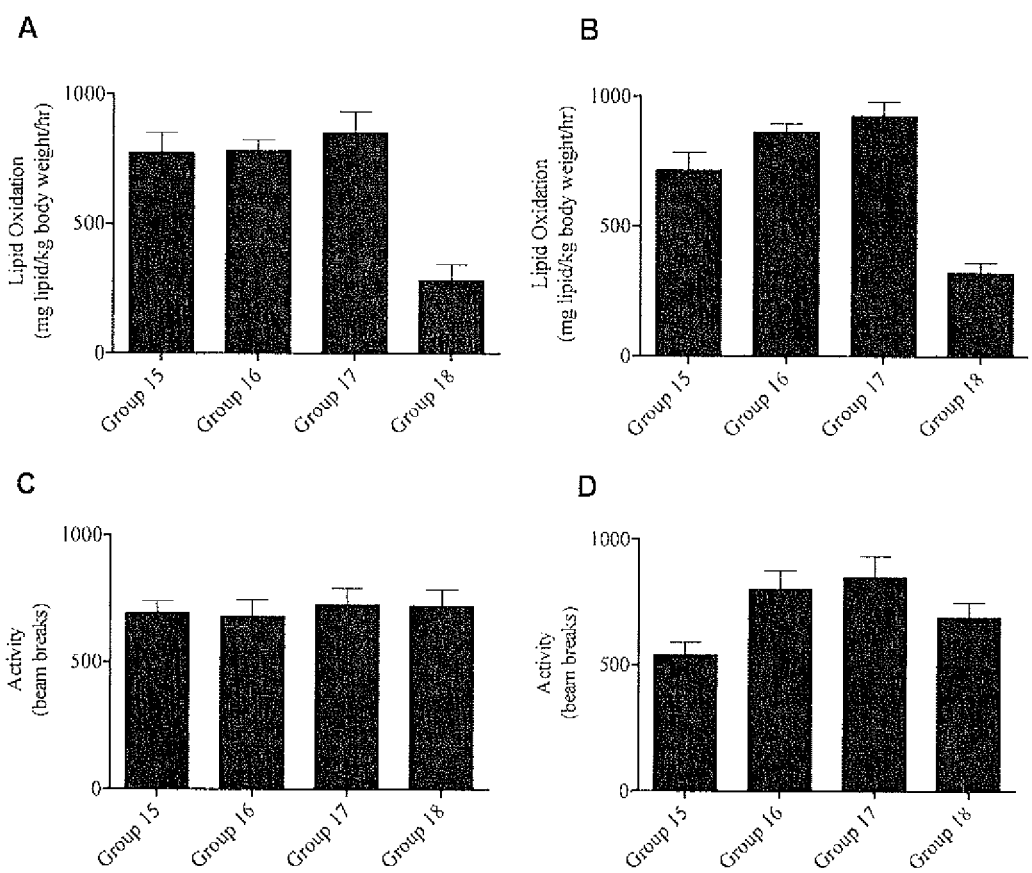
FIG. 21 graphically illustrates: lipid oxidation rates at: A) day −1 and B) day 1-3; and activity levels at: C) day −1 and D) day 1-3 of mice fed various formulations of a weight management composition or a control diet and evaluated in metabolic cages for 3 days.

21A). As would be expected, the fat oxidation rates of the Chow diet fed Group 18 were approximately 65% lower due to the low fat content of their diet. Following the 3 day treatment period, the average fat oxidation rates were 21% and 29% higher for Groups 16 and 17 fed the Weight management combination diets A and C respectively, when compared to the HFD fed Group 15 (FIG. 21B). Activity levels were also measured and showed all four groups having a similar activity levels during Day −1 (FIG. 21C). Interestingly, during the 3 day treatment period, activity levels of Groups 16-18 were all considerably higher than the HFD fed Group 15 (FIG. 21D). While not wishing to be bound by any particular mechanism, these findings suggest that two of the ways in which the weight management composition promote weight management is by increasing basal fat oxidation rates to promote fat loss and increasing physical activity to promote energy expenditure more generally.

Collectively, the findings from this study surprisingly reveal that the administration of the weight management composition comprising a weight loss agent and a mitochondria enhancing agent to an individual, or to an individual performing regular exercise, is an effective strategy for improving weight management, mitochondrial capacity, fatty liver disease, dyslipidemia, oxidative stress levels, brown adipose tissue activity and systemic inflammation levels in an individual.

The present compositions and methods advantageously provide individuals with a means for achieving weight loss, with or without performing exercise or dieting. In addition, the present weight management composition has been scientifically validated and permits use by individuals without the expenditure of time to determine which supplements should be used and will provide a desired beneficial effect. The present method and composition also provides health benefits to an individual in need thereof that are synergistic with the health benefits obtained from exercise.

The invention claimed is:

1. A weight management composition for use in a mammal comprising a daily dosage of 50-1000 mg of green tea extract, 50-1000 mg of green coffee bean extract, 15 mg-100 mg of forskolin, 50-5000 mg of beetroot extract, 50-900 mg of coenzyme Q10, 50 mg-900 mg alpha lipoic acid and 50-900 mg of vitamin E, and the amount of each of the components in the composition essentially corresponds to a ratio of: 0.375-1 green tea extract:0.25-1 green coffee bean extract:0.01-0.1 forskolin:1 beetroot extract:0.25-0.4 coenzyme Q10:0.1-0.8 alpha lipoic acid:0.2-0.4 vitamin E and is selected to result in a reduction of fat mass of at least 1% and to essentially maintain lean mass in the mammal.

2. The composition of claim 1, wherein the composition additionally comprises one or more selected from the group consisting of psyllium, guar gum, capsaicin, chitosan, caffeine, *Garcina cambogia, Pinus densiflora*, yohimbe, hoodia, glucomannan, African mango, guarana, pyruvate, carnitine, beta-glucans, fucoxanthin, raspberry ketone, white kidney bean, kola nut, chromium, ginseng, St. John's wort, dandelion, hydroxycitric acid, conjugated linoleic acid, black tea extract, bitter orange and mixtures thereof.

3. The composition of claim 1, wherein the composition additionally comprises black tea extract and conjugated linoleic acid.

4. The composition of claim 1, wherein the composition additionally comprises one or more selected from the group consisting of: nitrates, idebenone, nicotinamide riboside, elamipretide, vitamin C, vitamin D, thiamine, riboflavin, magnesium, calcium, phosphate, membrane phospholipids, creatine, pyruvate, NADH, nicotinic acid, L-carnitine, dichloroacetate, curcumin, schisandrin, resveratrol and mixtures thereof.

5. The composition of claim 1, wherein the composition additionally comprises creatine.

6. The composition of claim 1, additionally comprising one or more additional ingredients selected from proteins, carbohydrates, lipids, fibre, vitamins, minerals, antioxidants, prebiotics, probiotics, phytochemicals and phytonutrients.

7. The composition of claim 1, which is decaffeinated.

8. The composition of claim 1, formulated for oral administration.

9. A kit comprising two different dosage forms, a first dosage form comprising a weight loss agent and a second dosage form comprising a mitochondria enhancing agent, wherein the weight loss agent comprises 50-1000 mg of green tea extract, 50-1000 mg of green coffee bean extract and 15 mg-100 mg of forskolin and the mitochondria enhancing agent comprises 50-5000 mg of beetroot extract, 50-900 mg of coenzyme Q10, 50 mg-900 mg alpha lipoic acid and 50-900 mg of vitamin E, and the amount of each of the components in the first and second dosage forms essentially corresponds to a ratio of: 0.375-1 green tea extract: 0.25-1 green coffee bean extract:0.01-0.1 forskolin:1 beetroot extract:0.25-0.4 coenzyme Q10:0.1-0.8 alpha lipoic acid:0.2-0.4 vitamin E and is selected to result in a reduction of fat mass of at least 1% and to essentially maintain lean mass in a mammal.

10. A method for promoting weight management in a mammal comprising the step of administering to the mammal a composition as defined in claim 1.

11. The method of claim 10, wherein the weight loss agent additionally comprises one or more selected from the group consisting of psyllium, guar gum, capsaicin, chitosan, caffeine, *Garcina cambogia, Pinus densiflora*, yohimbe, hoodia, glucomannan, African mango, guarana, pyruvate, carnitine, beta-glucans, fucoxanthin, raspberry ketone, white kidney bean, kola nut, chromium, ginseng, St. John's wort, dandelion, hydroxycitric acid, conjugated linoleic acid, black tea extract, bitter orange and mixtures thereof, and the mitochondria enhancing agent additionally comprises one or more selected from the group consisting of: nitrates, idebenone, nicotinamide riboside, elamipretide, vitamin C, vitamin D, thiamine, riboflavin, magnesium, calcium, phosphate, membrane phospholipids, creatine, pyruvate, NADH, nicotinic acid, L-carnitine, dichloroacetate, curcumin, schisandrin, resveratrol and mixtures thereof.

12. The method of claim 10, wherein the composition additionally comprises a daily dosage of 50-500 mg of black tea extract, 500 mg-3 g of conjugated linoleic acid and 1-5 g of creatine.

13. The method of claim 10, wherein the composition is administered once daily.

14. The method of claim 10, wherein the composition is administered in portions two or more times daily.

15. The method of claim 10, wherein the weight loss agent is administered in a first dosage form and the mitochondria enhancing agent is administered in a second dosage form.

16. The method of claim 10, wherein the mammal additionally exercises.

17. A method to treat at least one of the following in a mammal: body weight, body fat, mitochondrial capacity, fatty liver disease, dyslipidemia, oxidative stress levels, brown adipose tissue activity and systemic inflammation levels comprising administering to the mammal a composition as defined in claim 1.

18. The composition of claim 1, additionally comprising a daily dosage of 50-500 mg of black tea extract, 500 mg-3 g of conjugated linoleic acid and 1-5 g of creatine.

19. The composition of claim 1, comprising a daily dosage of 250-1000 mg of green tea extract, 250-1000 mg of green coffee bean extract, 25 mg-100 mg of forskolin, 250-1000 mg of beetroot extract, 100-400 mg of coenzyme Q10, 150 mg-850 mg alpha lipoic acid and 100-400 mg of vitamin E.

20. The kit of claim 9, wherein the first dosage form comprises 250-1000 mg of green tea extract, 250-1000 mg of green coffee bean extract and 25 mg-100 mg of forskolin, and the second dosage form comprises 250-1000 mg of beetroot extract, 100-400 mg of coenzyme Q10, 150 mg-850 mg alpha lipoic acid and 100-400 mg of vitamin E.

21. The composition of claim 1, wherein the amount of each of the components in the composition essentially corresponds to a ratio of:1 green tea extract:1 green coffee bean extract:0.1 forskolin:1 beetroot extract:0.4 coenzyme Q10:0.8 alpha lipoic acid:0.4 vitamin E.

22. The kit of claim 9, wherein the amount of each of the components in the composition essentially corresponds to a ratio of: 1 green tea extract:1 green coffee bean extract:0.1 forskolin:1 beetroot extract:0.4 coenzyme Q10:0.8 alpha lipoic acid:0.4 vitamin E.

* * * * *